US012797626B2

(12) United States Patent
Peterchev et al.

(10) Patent No.: US 12,797,626 B2
(45) Date of Patent: Nov. 17, 2026

(54) METHODS AND SYSTEMS FOR MAGNETIC STIMULATION

(71) Applicant: Duke University, Durham, NC (US)

(72) Inventors: Angel Vladimirov Peterchev, Durham, NC (US); Lari Mikael Koponen, Coventry (GB); Stefan M. Goetz, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 1375 days.

(21) Appl. No.: 17/477,095

(22) Filed: Sep. 16, 2021

(65) Prior Publication Data

US 2022/0080217 A1 Mar. 17, 2022

Related U.S. Application Data

(60) Provisional application No. 63/079,182, filed on Sep. 16, 2020.

(51) Int. Cl.
*A61N 2/00* (2006.01)
*A61N 2/02* (2006.01)

(52) U.S. Cl.
CPC ............... *A61N 2/006* (2013.01); *A61N 2/02* (2013.01)

(58) Field of Classification Search
CPC .................................. A61N 2/006; A61N 2/02
USPC ........................................................ 600/9–15
See application file for complete search history.

(56) References Cited

U.S. PATENT DOCUMENTS

| | | | |
|---|---|---|---|
| 6,503,187 B1 | | 1/2003 | Ilmoniemi et al. |
| 6,564,900 B1 * | | 5/2003 | Dean .................. G01R 33/3854 381/71.2 |
| 10,471,272 B2 | | 11/2019 | Goetz et al. |
| 2001/0031906 A1 * | | 10/2001 | Ishikawa ................. H01F 7/064 600/13 |
| 2010/0113959 A1 * | | 5/2010 | Pascual-Leone ...... A61N 2/008 600/13 |
| 2015/0190648 A1 * | | 7/2015 | Fischell ................. A61N 2/006 600/14 |
| 2015/0367141 A1 * | | 12/2015 | Goetz ...................... A61N 2/02 600/14 |
| 2017/0189710 A1 | | 7/2017 | Goetz et al. |
| 2019/0269931 A1 * | | 9/2019 | Riehl ..................... A61N 2/006 |

OTHER PUBLICATIONS

Koponen et al., "Sound comparison of seven TMS coils at matched stimulation strength," Brain Stimulation, vol. 13, pp. 873-880 (2020).

(Continued)

*Primary Examiner* — Sunita Reddy
(74) *Attorney, Agent, or Firm* — Talem IP Law, LLP

(57) ABSTRACT

Methods and systems for magnetic stimulation are described. In some examples, a coil assembly for magnetic stimulation includes a winding block, a coil in the winding block, and a casing enclosing the winding block. The winding block is mounted to the casing only at one or more acoustic nodes of the winding block. The one or more acoustic nodes are identified as points in the winding block having minimal amplitude of vibrations when mechanically excited.

16 Claims, 13 Drawing Sheets

(56) References Cited

OTHER PUBLICATIONS

Jodoin et al., "Safety and Efficacy of Accelerated Repetitive Transcranial Magnetic Stimulation Protocol in Elderly Depressed Unipolar and Bipolar Patients," Am J of Geriatric Psychiatry, vol. 27, No. 5, pp. 548-558 (2019).
Liu et al., "Noise analysis and active noise control strategy of transcranial magnetic stimulation device," AIP Advances, vol. 9, pp. 1-11 (2019).
Miron et al., "Safety, tolerability and effectiveness of a novel 20 Hz rTMS protocol targeting dorsomedial prefrontal cortex in major depression: An open-label case series," Brain Stimulation, vol. 12, pp. 1319-1321 (2019).
Koponen et al., "Coil optimisation for transcranial magnetic stimulation in realistic head geometry," Brian Stimulation, vol. 10, pp. 1-11 (2017).
Folmer et al., "Hearing Protective Devices Should Be Used by Recipients of Repetitive Transcranial Magnetic Stimulation," Journal of Clinical Neurophysiology, vol. 34, No. 6, pp. 552 (Nov. 2017).
Kukke et al., "Hearing safety from single- and double-pulse transcranial magnetic stimulation in children and young adults," J Clin Neurophysiol., vol. 34, No. 4, pp. 1-16 (Jul. 2017).
"Recommended Practices for Safety and Health Programs," OSHA Occupational Safety and Health Administration, pp. 1-40 (Oct. 2016).
Vu et al., "A Low-Power Broad-Bandwidth Noise Cancellation VLSI Circuit Design for In-Ear Headphones," IEEE Transactions on Very Large Scale Integration (VLSI) Systems, vol. 24, No. 6, pp. 2013-2025 (Jun. 2016).
Vu et al., "Corrections to 'A Low-Power Broad-Bandwidth Noise Cancellation VLSI Circuit Design for In-Ear Headphones,'" IEEE Transactions on Very Large Scale Integration (VLSI) Systems, vol. 24, No. 6, pp. 2412 (Jun. 2016).
Braack et al., "Masking the Auditory Evoked Potential in TMS-EEG: A Comparison of Various Methods," Brain Topogr, vol. 28, pp. 520-528 (2015).
"Acoustical Standards News," The Journal of Acoustical Society of America, vol. 138, pp. 1-10 (Jul. 23, 2015).
"Department of Defense Design Criteria Standard Noise Limits," MIL-STD-1474E, pp. 1-123 (Apr. 15, 2015).
Koponen et al., "Minimum-energy Coils for Transcranial Magnetic Stimulation: Application to Focal Stimulation," Brain Stimulation, vol. 8, pp. 124-134 (2015).
Nieminen et al., "Experimental Characterization of the Electric Field Distribution Induced by TMS Devices," Brain Stimulation, vol. 8, pp. 582-589 (2015).
Peterchev et al., "Quiet transcranial magnetic stimulation: status and future directions," IEEE, pp. 1-4 (2015).
Schlittmeier et al., "The impact of road traffic noise on cognitive performance in attention-based tasks depends on noise level even within moderate-level ranges," Noise & Health, vol. 17, No. 76, pp. 1-17 (May-Jun. 2015).
Goetz et al., "Transcranial Magnetic Stimulation Device with Reduced Acoustic Noise," IEEE Magnetics Letters, vol. 5, pp. 1-4 (2014).
Goetz et al., "Impulse Noise of Transcranial Magnetic Stimulation: Measurement, Safety, and Auditory Neuromodulation," Letters to the Editor/Brain Stimulation, vol. 8, pp. 161-163 (2014).
Deng et al., "Electric field depth—focality tradeoff in transcranial magnetic stimulation: Simulation comparison of 50 coil designs," Brain Stimulation, vol. 6, pp. 1-13 (2013).
Peterchev et al., "Pulse width dependence of motor threshold and input-output curve characterized with controllable pulse parameter transcranial magnetic stimulation," Clinical Neurophysiology, vol. 124, pp. 1364-1372 (2013).
Schraven et al., "Hearing safety of long-term treatment with theta burst stimulation," Brain Stimulation, vol. 6, No. 4, pp. 1-23 (2013).
"ACGIH Threshold Limit Values (TLVs) and Biological Exposure Indices (BEIs)," TLVs and BEIs Based on the Documentation of the Threshold Limit Values for Chemical Substances and Physical Agents & Biological Exposure Indices, Appendix B, pp. 1-260 (2012).
Nelisse et al., "Measurement of Hearing Protection Devices Performance in the Workplace during Full-Shift Working Operations," Ann. Occup. Hyg., vol. 56, No. 2, pp. 1-13 (2012).
Smith, "Real-World Attenuation of Foam Earplugs," Science & Technology Watch, Aviation, Space, and Environmental Medicine, vol. 81, No. 7, pp. 696-697 (Jul. 2010).
Rossi et al., "Safety, ethical considerations, and application guidelines for the use of transcranial magnetic stimulation in clinical practice and research," Clin Neurophysiol., vol. 120, No. 12, pp. 1-69 (Dec. 2009).
Ilmoniemi, "The Triangle Phantom in Magnetoencephalography," The Journal of Japan Biomagnetism and Bioelectromagnetics Society, vol. 22, No. 1, pp. 1-3 (2009).
Zaehle et al., "Induction of LTP-like changes in human auditory cortex by rapid auditory stimulation: An FMRI study," Restorative Neurology and Neuroscience, vol. 25, pp. 251-259 (2007).
Martin et al., "Noise as a Trigger for Headaches: Relationship Between Exposure and Sensitivity," Headache, vol. 46, pp. 962-972 (2006).
Neitzel et al., "Variability of Real-World Hearing Protector Attenuation Measurements," Ann. Occup. Hyg., vol. 50, No. 7, pp. 679-691 (2006).
Wöber et al., "Trigger factors of migraine and tension-type headache: experience and knowledge of the patients," J Headache Pain, vol. 7, pp. 188-195 (2006).
Bestmann et al., "BOLD MRI responses to repetitive TMS over human dorsal premotor cortex," Neuroimage, vol. 28, pp. 22-29 (2005).
Clapp et al., "Induction of LTP in the human auditory cortex by sensory stimulation," European Journal of Neuroscience, vol. 22, pp. 1-12 (2005).
Massimini et al., "Breadown of Cortical Effective Connectivity During Sleep," Science, vol. 309, pp. 1-6 (Sep. 2005).
Zangen et al., "Transcranial magnetic stimulation of deep brain regions: evidence for efficacy of the H-Coil," Clinical Neurophysiology, vol. 116, pp. 775-779 (2005).
Toivonen et al., "Noise Attenuation and Proper Insertion of Earplugs into Ear Canals," Ann. Occup. Hyg., vol. 46, No. 6, pp. 527-530 (2002).
Paus et al., "Synchronization of Neuronal Activity in the Human Primary Motor Cortex by Transcranial Magnetic Stimulation: An EEG Study," The American Physiological Society, pp. 1983-1990 (2001).
Nikouline et al., "The role of the coil click in TMS assessed with simultaneous EEG," Clinical Neurophysiology, vol. 110, pp. 1325-1328 (1999).
Starck et al., "The Noise Level in Magnetic Stimulation," Scandinavian Audiology, vol. 25, No. 4, pp. 1-7 (1996).
Kamon et al., "FastHenry: A Multipole-Accelerated 3-D Inductance Extraction Program," 30th ACM/IEEE Design Automation Conference, pp. 1-6 (1993).
Barker et al., "Magnetic Nerve Stimulation: the Effect of Waveform on Efficiency, Determination of Neural Membrane Time Constants and the Measurement of Stimulator Output," Magnetic Motor Stimulation: Basic Principles and Clinical Experience, pp. 1-9 (1991).
Berger, "Methods of measuring the attenuation of hearing protection devices," J. Acoust. Soc. Am., vol. 79, No. 6, pp. 1-35 (Feb. 14, 1986).
McGee et al., "Combining Rules for Predicting the Thermoelastic Properties of Particulate Filled Polymers, Polyblends, and Foams," Polymer Composites, vol. 2, No. 4, pp. 149-162 (Oct. 1981).

* cited by examiner

METHODS AND SYSTEMS FOR MAGNETIC STIMULATION

PRIORITY CLAIM

This application claims the benefit of U.S. Provisional Patent Application Ser. No. 63/079,182, filed Sep. 16, 2020, the disclosure of which is incorporated herein by reference in its entirety.

GOVERNMENT INTEREST

This invention was made with government support under MH111865 awarded by the National Institutes of Health. The government has certain rights in the invention.

TECHNICAL FIELD

The subject matter described herein relates generally to magnetic stimulation. More particularly, the subject matter described herein relates to methods and systems for quiet transcranial magnetic stimulation.

BACKGROUND

Transcranial magnetic stimulation (TMS) is a noninvasive method for brain stimulation, with both clinical and research applications. In TMS, an electromagnet coil placed on the subject's scalp is pulsed to create a rapidly changing magnetic field (B-field) which induces an electric field (E-field) in the vicinity of the coil. A typical biphasic TMS pulse lasts only about 300 μs, but must produce peak magnetic field on the order of 1 T, which requires a coil current over 1000 A. The high current and magnetic field produce a mechanical vibration of the coil, which manifests itself in a loud, impulsive sound. The peak sound pressure level (SPL) can exceed 130 dB (Z), and the continuous sound level (SL) during a repetitive TMS (rTMS) pulse train can exceed 110 dB (A), where (Z) refers to flat frequency weighting and (A) designates the most common perceived loudness weighting that emphasizes frequencies between 1 and 6 KHz.

SUMMARY

The methods and systems described in this document can be used to reduce the acoustic noise level of transcranial magnetic stimulation (TMS) coils. TMS requires high currents (several thousand amperes) to be pulsed through the coil, which generates a loud acoustic impulse whose peak sound pressure level (SPL) can exceed 130 dB (Z). This sound poses a risk to hearing and elicits unwanted neural activation of auditory brain circuits.

To avoid transmission of mechanical vibrations between the windings and the exterior surface of the coil, the invention mounts the windings to the casing in a manner that is at the same time stiff enough—to hold the relatively heavy windings in place at a minimal distance from the head under normal handling— and suitably mechanically decoupled from transmitting the inevitable vibrations of the windings to the outer surfaces of the coil—from which they would get transmitted to surrounding air as sound. In some embodiments, the coil arrangements according to the present disclosure incorporate designs of the windings in such a way, that they contain multiple points with little-to-no vibration, i.e., nodal points, and mount the windings only from these points to the outer casing. These nodal points are points in the windings where the amplitude of vibrations is minimal when the windings are mechanically excited. This can, particularly, include mechanical standing waves, which are also often called mechanical modes or short modes of an object. As the strong current pulses in adjacent turns of the stimulation coil with above-given frequency range lead to the electromagnetic forces that excite the vibrations of the windings, which subsequently emit as sound from the surface, their frequency determines the mechanical excitation of the body. The frequency range of the current pulses therefore typically excites mechanical vibrations in a frequency range that leads to wavelengths that are on the size order of the windings (a majority not longer than 20 times and not shorter than 1/20-th of the dimensions of the windings, particularly, its longest dimension) and standing waves or mechanical modes. Each such mode has distinct nodal lines or points. The nodal points show smallest amplitude and therefore also smallest velocity, which is required to effectively transfer the mechanical vibration to other bodies, which in some embodiments of the present disclosure include the casing.

BRIEF DESCRIPTION OF THE DRAWINGS

FIG. 1I is a block diagram of an example system for magnetic stimulation;

DETAILED DESCRIPTION

Figure 1A:
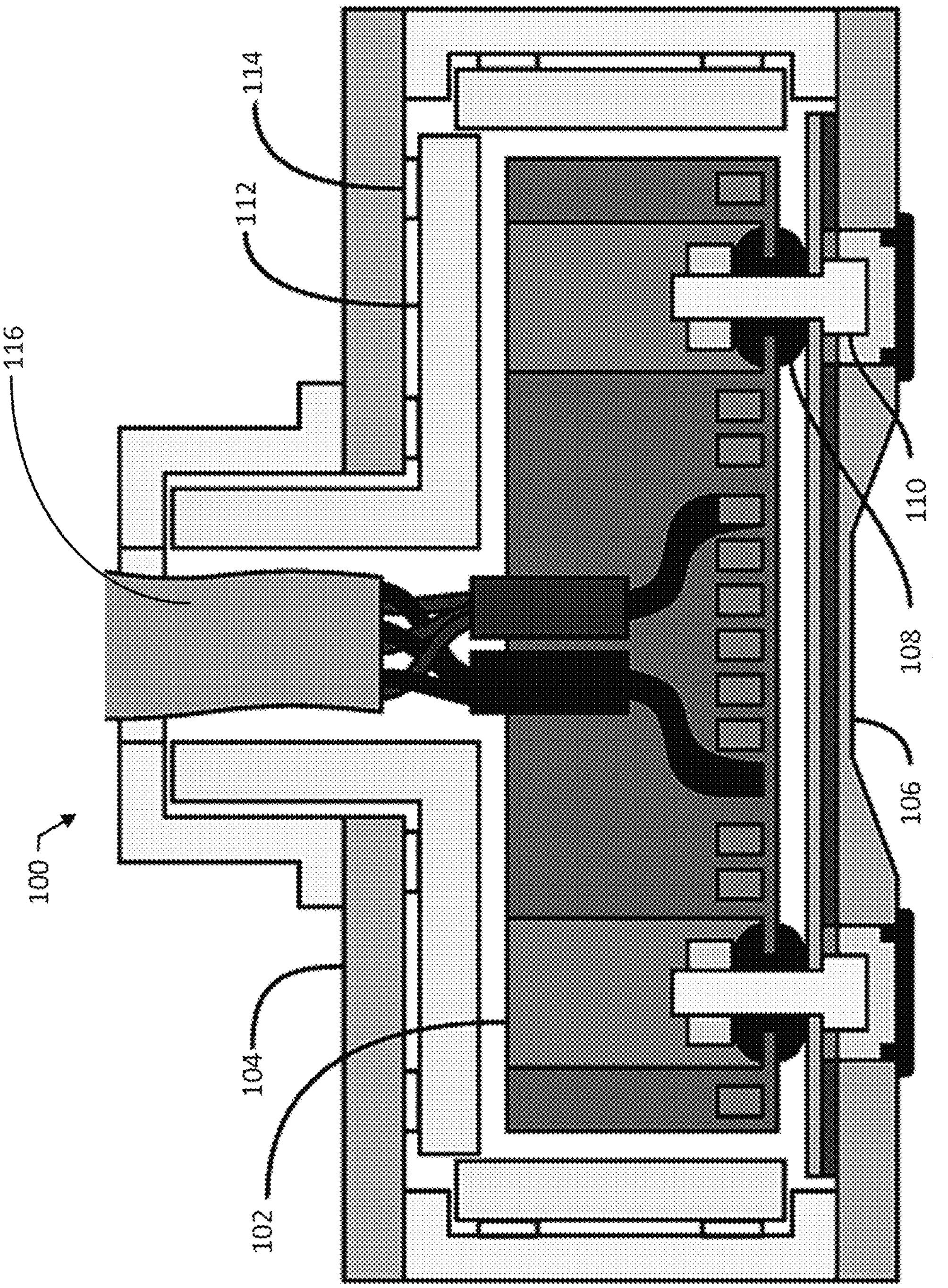
FIG. 1A shows an example coil assembly.

Transcranial magnetic stimulation (TMS) is a noninvasive method for brain stimulation, with both clinical and research applications. In TMS, an electromagnet coil placed on the subject's scalp is pulsed to create a rapidly changing magnetic field (B-field) which induces an electric field (E-field) in the vicinity of the coil. A typical biphasic TMS pulse lasts only about 300 μs, but must produce peak magnetic field on the order of 1 T, which requires a coil current over 1000 A. The high current and magnetic field produce a mechanical vibration of the coil, which manifests itself in a loud, impulsive sound. The peak sound pressure level (SPL) can exceed 130 dB (Z), and the continuous sound level (SL) during a repetitive TMS (rTMS) pulse train can exceed 110 dB (A), where (Z) refers to flat frequency weighting and (A)

designates the most common perceived loudness weighting that emphasizes frequencies between 1 and 6 KHz [1], [2].

The coil sound is a significant limitation of TMS. It poses a risk to hearing [1], [3]-[5] and, with missing or inadequate hearing protection, can cause permanent hearing damage [6]. The loud sound contributes to several adverse side effects of TMS [3], such as headaches [7], [8], and reduces the effective focality since auditory pathways are activated synchronously with the electromagnetic stimulation [9], [10]. During rTMS, the acoustic stimulation further risks unwanted neuromodulation [11], [12].

There are several adopted or proposed approaches to mitigate the effects of the TMS sound. For safety purposes [3], [5], [13], [14], adequate hearing protection during TMS can be obtained with either earmuffs (typical attenuation 20-30 dB for relevant frequencies, i.e., above 1 kHz [15]) or correctly worn earplugs (typical attenuation 20-25 dB for the same frequencies [15]). A consistently good fit of earplugs, though, can be challenging to obtain for all subjects [16]-[19]. Indeed, the reported case of permanent hearing damage from TMS was likely due to incorrectly applied earplugs [6]. Hearing protection devices, even when applied correctly, do not reduce the sound level sufficiently to mitigate the other side effects of the loud sound. Beyond hearing protection, the perceived sound can be reduced with a layer of foam between the coil and the scalp to decrease bone-conduction of the sound [9], [20]. This added distance between the coil and the head, however, reduces both the energy efficiency and attainable stimulation focality-if the coil winding is not optimized for the extra spacing, the efficiency loss is about 10% per mm [21].

In principle, active noise cancellation (ANC) technology could reduce the sound intensity reaching the cochlea. Conventional real-time ANC solutions, however, are typically limited to steady-state sounds and lower frequencies, providing attenuation only for frequencies below 1 kHz, even with in-ear headphones and for sound intensities much lower than TMS [22], [23]. The TMS coil click has peak SPL that would require extremely powerful headphones, and contains mostly frequencies that are too high for ANC. A TMS-specific offline ANC solution could theoretically solve the problem with high frequencies, but even in simulations, the attenuation for frequencies above 1 kHz was rendered close to zero with a small change in the coil orientation [24]. An ANC solution would also not reduce the bone-conducted sound. Importantly, none of the approaches described so far are sufficient to prevent auditory brain activation.

Consequently, noise played through earphones, e.g. fixed 90 dB (A) or individually-leveled white noise, is sometimes used to mask the TMS sound [25], [26]. By practically raising the hearing threshold, such noise masking can reduce unwanted TMS-synchronized auditory activation. However, the loud masking sound itself may disturb noise-sensitive subjects and patients; hinder verbal communication, auditory tasks, or psychotherapy during the TMS session; reduce cognitive performance [27]; and require noise dosimetry to ensure adhering to hearing safety limits [28], [29].

Considering the adverse impact of the loud TMS sound and the limitations of mitigation approaches, it is compelling to develop TMS devices with lower acoustic emissions. This approach is further supported by the conventional hierarchy of hazard controls, in which personal protective equipment is considered the least effective, last-resort solution [30]. Prior to this work, three methods to reduce the sound have been suggested: The sound could be contained by placing the coil inside a medium-to-high vacuum of below 1 Pa [31]. However, such containment would greatly increase the distance between the coil and the head, which would require much more powerful stimulators and pose considerable problems with cooling.

Instead, some commercial MRI-compatible coils use up to 10 mm of acoustic foam to separate the windings from the exterior, which results in a lower sound level, but still at the price of some loss in maximum output and focality [1], [32]. To further reduce the thickness of the sound insulation, our earlier work suggested impeding the sound transmission with multiple layers of different materials: a stiff winding block in a viscoelastic bed, surrounded by an elastic silicone layer and a stiff outer casing [33]. This approach allowed reduced sound while having separation between the winding and the coil surface (4-6 mm) comparable to the upper range for conventional coils (2-5 mm). This coil design was part of a previous proposed two-pronged approach to "quiet TMS," involving improved electro-mechanical coil design and the use of briefer pulses [33], [34].

This document describes an improvement upon the electromechanical coil design for quiet TMS. A double-containment coil (DCC) design is described in which a stiff, electromagnetically-optimized winding block is surrounded by an air cavity—as opposed to solid materials or vacuum—to minimize the sound transmission to the casing. Further, the mounting points of the winding block are designed to have minimal vibrations due to TMS. Finally, the casing has appropriate stiffness and absorption properties, while minimizing the distance between the winding and the subject's head. Computational and experimental measurements of the coil electromagnetic and acoustic output are presented, including a comparison with commercial TMS coils.

The present disclosure provides a stimulation coil arrangement for pulsed magnetic stimulation that comprises, consists of, or consists essentially of at least two key parts: (a) coil windings of suitable design including their geometry and construction as described herein (also referred to as the winding assembly or short the windings of the coil—which refers to both the actual conductive coil windings and the supporting material for these); and (b) a casing structure used to contain this winding assembly.

In general, the coil assembly described in this document includes a winding block and a coil potted in the winding block. The winding block can be formed of any appropriate material, e.g., potting epoxy. The coil includes several turns of a conductor, e.g., a solid metal conductor, such as copper or aluminum, a wound solid wire, or a wound litz wire. The windings of the coil can be, for example, spiral, planar, or bent. In some examples, solid or litz wire can be wound as a spiral with an inner diameter smaller than an outer diameter of the spiral.

The coil assembly includes a casing enclosing the winding block. The winding block is mounted to the casing at one or more acoustic nodes of the winding block that are subject to a minimum vibration during a magnetic stimulation pulse, e.g., a pulse appropriate for transcranial magnetic stimulation. The acoustic nodes can be identified, e.g., by computer modeling or by testing or using any appropriate method. Mounting the winding block at acoustic nodes can reduce the volume produced during magnetic stimulation.

Examples of the coil assembly and prototypes are described further below. This document describes examples and prototypes for purposes of illustration and not for purposes of limitation.

Materials and Methods

Coil Structure

FIG. 1A shows an example coil assembly 100. The coil assembly 100 has a double-containment structure, in which a potted optimized winding is contained within an independent stiff outer casing, separated from the winding block by an air gap (e.g., a 1.6 mm air gap) on the head-facing side and another air gap (e.g., a 17 mm air gap) on the other five sides. The purpose of this air gap is to create maximum acoustic impedance mismatch between the stiff winding block, which acts as a sound pressure source, and the stiff outer casing walls.

With this construction, most of the sound gets reflected off the interior surface of the outer casing, which delays the sound transmission and increases transmission losses. Consequently, sound pressure inside the outer casing gets amplified, whereas the sound pressure outside the outer casing gets attenuated. To minimize the duration of the sound, two thirds of the air gap on all but the head-facing side were filled with sound absorbing polyester fiber panels (e.g., 9 mm thick), mounted to the outer casing with an air gap (e.g., 2 mm air gap) for maximum effectiveness.

As shown in FIG. 1A, the coil assembly 100 includes a winding block 102, which is essentially a fully-fledged TMS coil, and an outer casing 104 with a lid (bottom) with a central recession 106 to reduce the winding-to-head distance.

To avoid transmission of mechanical vibrations between the windings and the exterior surface of the coil, the invention mounts the windings to the casing in a manner that is at the same time stiff enough—to hold the relatively heavy windings in place at a minimal distance from the head under normal handling— and suitably mechanically decoupled from transmitting the inevitable vibrations of the windings to the outer surfaces of the coil—from which they would get transmitted to surrounding air as sound. In some embodiments, the coil arrangements according to the present disclosure incorporate designs of the windings in such a way, that they contain multiple points with little-to-no vibration, i.e., nodal points, and mount the windings only from these points to the outer casing. These nodal points are points in the windings where the amplitude of vibrations is minimal when the windings are mechanically excited. This can, particularly, include mechanical standing waves, which are also often called mechanical modes or short modes of an object. As the strong current pulses in adjacent turns of the stimulation coil with above-given frequency range lead to the electromagnetic forces that excite the vibrations of the windings, which subsequently emit as sound from the surface, their frequency determines the mechanical excitation of the body. The frequency range of the current pulses therefore typically excites mechanical vibrations in a frequency range that leads to wavelengths that are on the size order of the windings (a majority not longer than 20 times and not shorter than 1/20-th of the dimensions of the windings, particularly, its longest dimension) and standing waves or mechanical modes. Each such mode has distinct nodal lines or points. The nodal points show smallest amplitude and therefore also smallest velocity, which is required to effectively transfer the mechanical vibration to other bodies, which in some embodiments of the present disclosure include the casing.

If either the mass of the coil is concentrated towards its perimeter, or if the coil windings are concentrated towards the center of the coil (but whilst retaining near uniform density distribution), the winding shows pairs of additional nodal points appearing near the perimeter of the coil. The latter, concentrating the windings towards the center has an additional benefit of increasing the energy-efficiency of the coil. For such a coil and according to one embodiment of the present disclosure, the winding can have two additional nodal points along the axis of symmetry connecting the two wings of the coil.

Figure 1B:
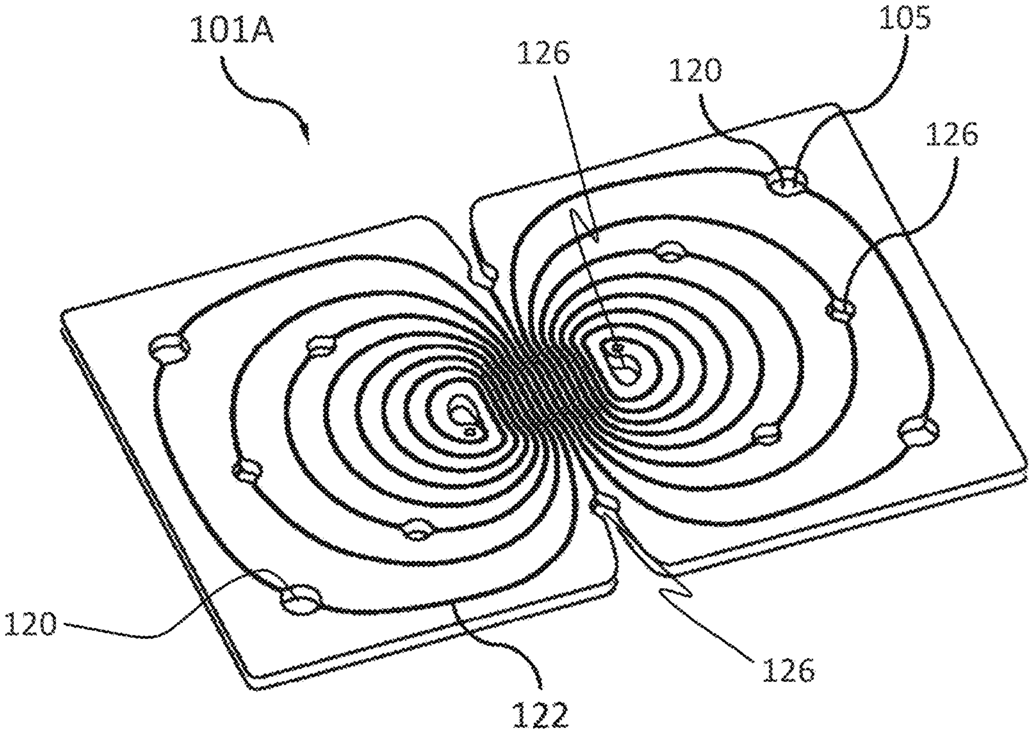
FIG. 1B is a schematic showing the coil windings of a winding assembly having four nodal points near the four corners in accordance with one embodiment of the present disclosure.
Figure 1C:
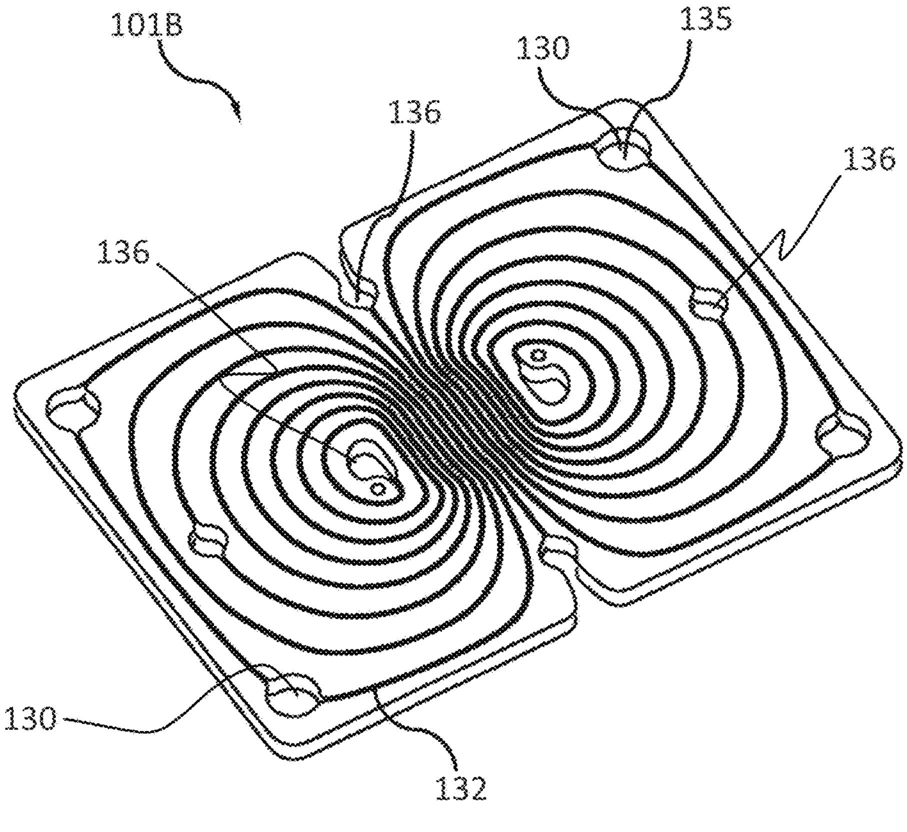
FIG. 1C is a schematic showing the coil windings of a winding assembly in accordance with one embodiment of the present disclosure.
Figure 1D:
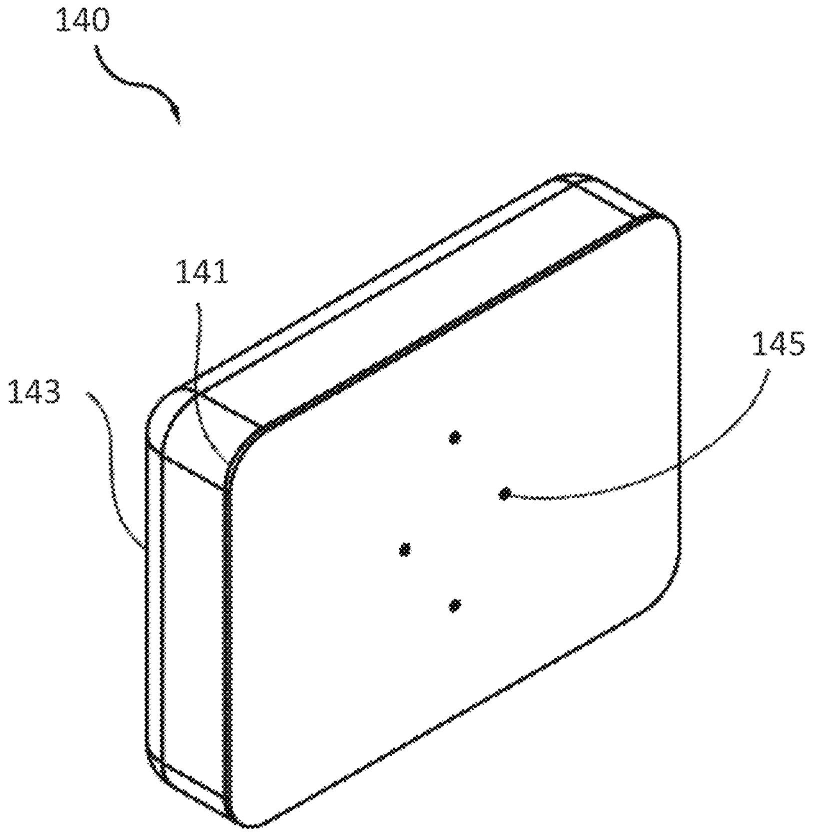
FIGS. 1D-1H are schematics of a coil and various cross-sectional views in accordance with one embodiment of the present disclosure.
Figure 1E:
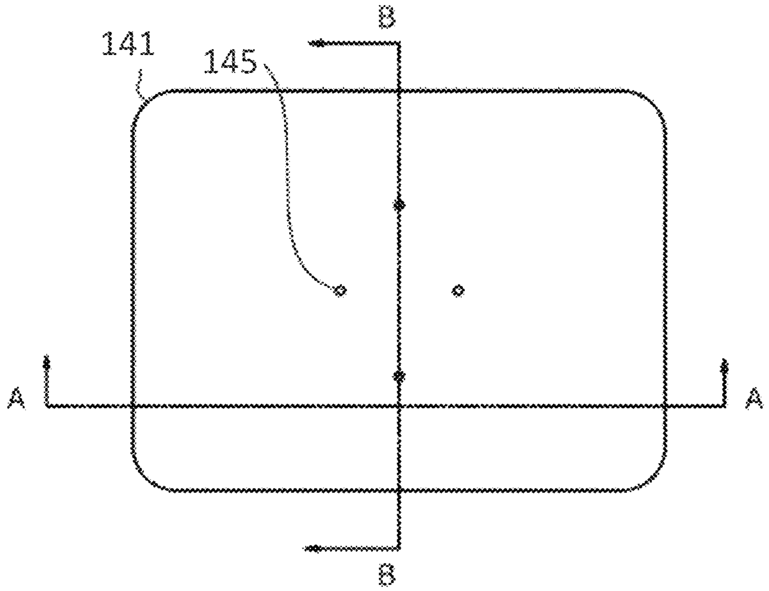
Figure 1F:
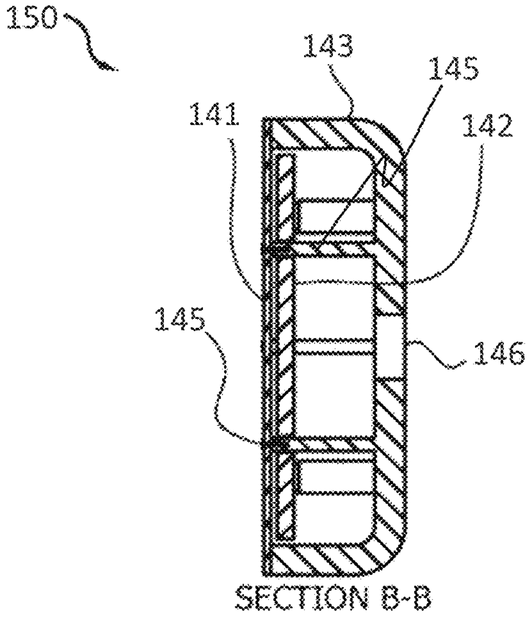
Figure 1G:
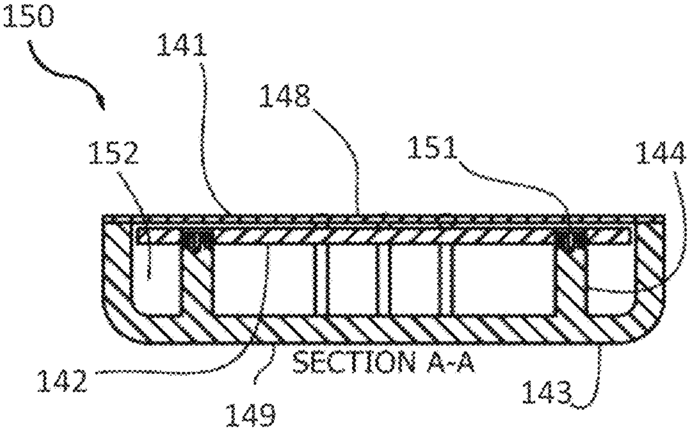

Alternatively, in certain embodiments, the winding can have four nodal points near the four corners of a rectangular coil (as is the case of the example embodiments shown in FIGS. 1B and 1C.

FIG. 1B is a schematic showing the coil windings of a winding assembly 101A having four nodal points 120 near the four corners in accordance with one embodiment of the present disclosure. In addition to the nodal points 120, the windings have room (see openings 126) for ten support beams for the lid (two in the centerline of the two wings of the Figure-of-eight-like coil, and four surrounding it on both wings). In the depicted coil windings 122, the width of the conductor considerably increases towards the perimeter, whereas the gaps between the turns remain constant; and FIG. 1C is a schematic showing the coil windings 132 of a winding assembly 101B in accordance with one embodiment of the present disclosure. The embodiment of FIG. 1C has openings 136 for six support beams for the lid (two in the centers of the two winds of the Figure-of-eight like coil, and four surrounding it from different sides). The windings are mounted from the four large holes 135 near its corners, which for these windings approximately correspond to the locations of the nodal points 130.

Referring again to FIG. 1A, the winding block 102 is mounted flexibly to the outer casing 104 with rubber grommets 108 and nylon bolts 110 at the point of minimal in-plane vibration. In general, any appropriate mounting structures can be used to mount the winding block 102.

According to one embodiment and as shown in FIGS. 1B and 1C, the winding assembly is mounted with rubber grommets at the holes (105, 135) for rubber grommets which have been particularly designed to be at the nodal points (120, 130). The approach can also be used to mount an existing set of coil windings: identify locations of small vibrations (if any) by simulating or measuring the spatiotemporal distribution of vibrations of the existing coil, and modify that region to allow mounting that coil as the windings inside an outer casing, e.g., by adding bolt or a place for a rubber grommet.

In other embodiments, the coil arrangement comprise further using the maximum amount of material where possible as it results in maximal stiffness and maximal density, both of which reduce the average extent of vibrations in the windings (see, e.g., Goetz et al., 2014, IEEE Magnetics Letters, 2014, 5(1500104):1-4. doi: 10.1109/LMAG.2014.2351776]. The same principle of generating or finding nodal points can be applied to lighter constructions [see, e.g., Koponen et al., 2017, Brain stimulation, 10 (4): 795-805].

To reduce reverberation, the outer casing walls not facing the head are covered with sound absorbing panels 112 mounted with, e.g., thick foam tape squares 114.

To minimize the distance to the winding on the head-facing side while retaining structural rigidity, the outer casing (lid) incorporated at its center a shallow circular recession (e.g., outer diameter 110 mm, inner diameter 70 mm, depth 4.0 mm) with a thickness of, e.g., only 2.4 mm (4.0 mm with the air gap). Based on simulations, such shallow recession does not interfere with placing the coil above any common stimulation location in a representative set of human head models. To minimize the sound transmission via the mounting points for the winding block, their locations were optimized to coincide with nodal points of minimum in-plane vibration of the winding block, determined from an electromechanical simulation. The mounting points were equipped with commercial styrene-butadiene rubber grommets to reduce further this mode of sound transmission via mechanical vibrations.

In some embodiments, the lid comprises a thickness of less than 10 mm, 9 mm, 8 mm, 7 mm, 6 mm, 5 mm, 4 mm, 3 mm, 2 mm, or 1 mm. In one embodiment, the lid comprises a thickness of less than or equal to 5 mm. In certain embodiments, the lid comprises a thickness of less than or equal to 2 mm. In certain embodiments, the lid forms the side facing a subject. In another embodiment, the at least one lid and the at least one winding assembly are separated by at least one air gap. In some embodiments, the at least one airgap between the at least one winding assembly and the at least one lid is between at least 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, and 10 mm thick in at least one dimension. In certain embodiments, the airgap between the at least one winding assembly and the at least one lid is between at least 0.5 mm and 5 mm thick in at least one dimension.

In other embodiments, mounting beams between the outer casing and the lid may reach through the winding assembly and the airgap, preferably without a mechanical connection to the winding assembly without foiling the nature of the airgap according to this invention. The embodiment may further comprise at least one second air gap between the at least one winding assembly and the at least one outer casing, wherein the latter may be filled with acoustic foam or similar material. In certain embodiments, the at least one winding assembly is mounted to the at least one outer casing at multiple nodal points of the mechanical modes of the at least one winding assembly, which as described above are areas with relatively small mechanical displacement during mechanical oscillations and vibrations in response to mechanical excitation. In another embodiment, the at least one winding assembly is mechanically mounted to multiple mounting pillars that extend from the at least one outer casing towards the at least one winding assembly, wherein the interface between the multiple mounting pillars and the at least one winding assembly is formed by elastic and/or viscoelastic material. Suitable materials include, but are not limited to, silicone or rubber. Furthermore, the winding assembly in such embodiments can comprise multiple holes large enough to let mounting beams between the at least one lid and the at least one outer casing pass without mechanical interaction. In other certain embodiments, the lid is preferably additionally mechanically connected to the at least one outer casing at least one interface formed by at least one edge of the at least one lid and at least one edge of the at least one outer casing.

Also shown in FIG. 1A is a power cord 116. The power cord 116 electrically connects to the at least one winding assembly and extends to the outside of the outer casing 104.

Figure 1H:
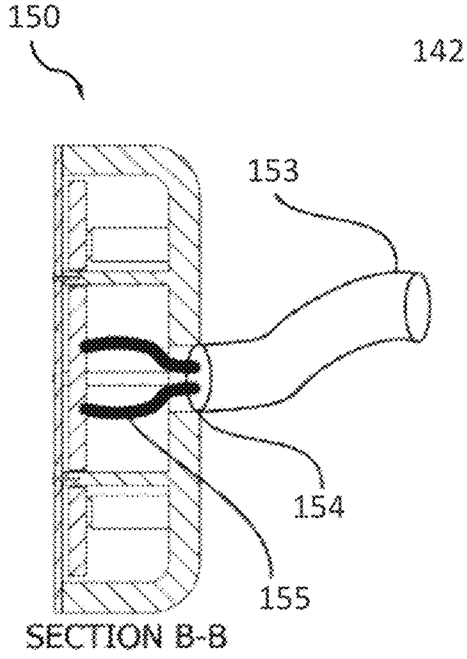

In another embodiment, at least one power cord comprises at least one cable jacket and is mechanically tightly connected to at least one outer casing with the at least one cable jacket, wherein the cable extends from the outer casing to the winding assembly and electrically connects to the winding assembly. In certain embodiments, the cable forms at least two sections with at least one section comprising the at least one cable jacket and at least one section without cable jacket, wherein the at least two sections differ in mechanical flexibility. In some embodiments, the difference in mechanical flexibility is at least a factor of 1, 2, 3, 4, 5. In certain embodiments, the difference in mechanical flexibility is by at least a factor of five. In another embodiment, the coil arrangement further comprises at least one cable section without cable jacket located between the at least one outer casing and the at least one winding assembly. In this embodiment, the at least one cable section without cable jacket can further be thinner than the at least one cable section that comprises at least one cable jacket, e.g., by at least a factor of two. The length of the cable section that extends from the outer casing to the winding assembly, which coincides with the power cord connection section (see, e.g., FIG. 1H, 155), is longer than the distance between the at least one point where the cable leaves the outer casing and the at least one point where the cable reaches the winding assembly. Accordingly, the cable section that extends from the outer casing to the winding assembly is advantageously designed such it does not experience mechanical tension. For instance, the cable section that extends from the outer casing to the winding assembly can be formed to an s-shaped path.

Another embodiment of the present disclosure, represented by FIGS. 1D-1H, provides schematics of a coil arrangement 140 according to the present disclosure and various cross-section views of such a coil arrangement. In one embodiment, the outer casing 143, comprises several support beams 145 that go through strategically added holes (147, also shown in, e.g., FIG. 1B, 126, and FIG. 1C, 136) in the windings 142, and consequently are not touching the windings 142. In FIGS. 1D-1H, and according to one embodiment, four such support beams 135 near the center are shown. Such a location prevents the lowest oscillation modes of the thin lid 141 of the TMS coil 150. In FIGS. 1B and 1C, in addition to the four support beams near the coil center, in these example embodiments two and six additional beams are located to suppress several further potential oscillation modes of the lid.

In certain embodiments, inside the coil, the windings are mounted from a few points near its periphery, ideally from its nodal points. This way the mounting points in the windings are already largely decoupled from the within-windings vibrations. The mounting can further be given additional degrees of freedom, both common engineering solutions (e.g., grommets), and nontrivial application specific designs like connecting the mounting points only to the far side of the coil (as shown in FIGS. 1D-1H). Unlike for the lid 141, the thicker wall in the outer casing 143 does not affect the efficiency of brain stimulation. Thus, the casing walls 143 can be made several times thicker than the lid 141 (at least three times thicker, preferably at least five times thicker; in the embodiments of FIGS. 1D-1H, the casing walls 143 are twelve times thicker and thus at least ten times thicker than the lid 141). This serves two purposes: The additional thickness (even if it is achieved with a hollow composite structure, such as a honeycomb composite) makes the outer walls stiffer; with different stiffness, the bottom and top surfaces of the coil do not share common vibration modes. The additional thickness can be used to add mass to further decouple the coil windings from exiting the outer surface of the coil near or within the winding-assembly mounting poles (FIGS. 1D-1H, three times thicker pillars 144 for the winding-assembly mount than for lid support beam 145, providing nine times the mass). In one embodiment, a conservatively selected 10-mm wall thickness was used (compared to 0.8 mm for the lid) to provide both additional mass and stiffness.

As shown in FIGS. 1D-1H, the head-side is formed by a thin, stiff lid 141, for example, from fiberglass, preferably laminated with typical polymer resins, such as epoxy. Following a key component of the invention, the lid is not directly connected to the winding assembly 142, rather, the two are separated by a thin air gap.

Again as shown in FIGS. 1D-1H, at least one mounting or support pillar 144 for the winding assembly 142 directly or preferably indirectly mechanically connects the windings 142 with the outer casing 143. To decouple the winding assembly 142 from the lid 141 on the subject side 148, the winding assembly has to be mostly supported from the back side 149 of the coil casing, i.e., the side opposite to the subject's head. In this embodiment, the winding assembly is further decoupled from the support pillars with rubber grommets, with the rubber grommets covering that part of the surface of the winding assembly that would touch the support pillar, forming a rubber interface 151, so that all mechanical vibrations have to travel through this rubber interface 151. The outer casing 143 as one part of the TMS coil is preferably mechanically stiff, e.g., made of an engineering plastic with a minimum E modulus of greater than 1 GPa. The embodiment in FIGS. 1D-1H depicts a large cavity or airgap on the back side 149 of the coil, which can be filled with acoustic foam to further dissipate the sound waves. In the prototype, a small cavity was used. The winding assembly 142 containing the coil windings (e.g., embodiments of the coil windings in the winding assembly as shown in FIG. 1B or 1C and described above).

In some embodiments, the coil arrangement further comprises multiple lid support beams 145, i.e., support beams for the lid, in this case four beams. The beams have no immediate mechanical connection or interface to the windings, but rather pass through holes 147 in the winding assembly, large enough to avoid mechanical interaction, without touching. The pulse current is delivered to the winding assembly 142 through at least one power cord 153, which extends out of the coil arrangement through the outer casing 143 or the lid 141. In certain embodiments, the at least one power cord 153 passes (e.g., via opening 146) through the outer casing 143 and is mechanically fixed (154) to the outer casing 143, wherein the section of the at least one power cord reaching from the outer casing 143 to the winding assembly 142 is longer than the distance between the at least one outer casing 143 and the at least one winding assembly 142.

A certain embodiment of the coil arrangement system according to the present disclosure, and as shown in FIGS. 1D-1H, comprises at least one winding assembly 142, at least one outer casing 143, at least one support pillar 144, which forms an interface with the winding assembly 142 through rubber grommets 151, at least one lid 141, at least one power cord 153, which is electrically connected to the winding assembly by a power cord connection section 155, and multiple lid support beams 145, which mechanically connect to the at least one lid 141 as well as to the at least one outer casing 143 and pass through the winding assembly 142 through holes 147 in the winding assembly 142. Such embodiments may further comprise at least one airgap between the lid 141 and the at least one winding assembly 142 and an air gap between the at least one winding assembly 142 and the outer casing 143 on the back side 149.

To a person skilled in the art, it is not obvious why such enclosure would indeed suppress the sound pressure, as it essentially looks like a loudspeaker with a planar diaphragm (the thin lid 141 being the diaphragm). The suppression is a result of maximal acoustic impedance mismatch between the air in the cavity 152 and either the relatively massive (all sides but the head side, i.e., the side facing the head of a subject during stimulation), or relative-to-air dense (the thin lid between the windings and the head) walls of the cavity. With this design, the initial loud sound impulse is mostly reflected back-and-forth between the winding assembly and the outer casing, which turns the sharp impulse into a prolonged impulse. This alone achieves considerable attenuation.

In another embodiment, the attenuation can further be reduced by conventional acoustic engineering methods, including filling the cavity on the back side 149 of the windings with open-cell acoustic foam, or an application-specific acoustic metamaterial, such as tuned anti-reflection wedges resembling scaled-down-variant of the wedges used in anechoic chambers, or other suitable acoustic-absorbing materials (see, e.g., Beranek et al., 1946, The Journal of the Acoustical Society of America, 18(1):140-50) but tuned to attenuate only the much-higher-frequency resonant modes present in the outer casing (the walls of a typical anechoic chamber attenuate frequencies from about 100 Hz or below, whereas in this case attenuation is needed only for frequencies >1,000 Hz).

In another embodiment of the present disclosure, the at least one winding assembly 142 comprises a coil winding 101A, 101B formed by solid wire or preferably litz wire that is wound to at least one spiral or spiral-like shape and potted with a stiff resin, such as epoxy, to a stiff, nonelastic object that preferably is planar or bent. Accordingly, in such embodiments the winding assembly can be manufactured through metal-cutting techniques such as water-jet cutting, laser cutting, and milling, wherein the individual turns are preferably formed by cutting along a line between two adjacent turns, and subsequent potting as described above, or winding of solid wire or litz wire and subsequent impregnation or potting. The winding assembly is either formed such as to comprise at least one hole 147 (126, 136), preferably at least three holes 147; or the at least one hole 147, preferably at least three holes 147, are formed subsequently by established processes, such as drilling or metal cutting. The winding assembly can be mounted onto a preformed outer casing 143 comprising at least one preformed winding-assembly support pillar 144, preferably at least three preformed winding-assembly support pillars 144, which preferably touch the winding assembly 142 at nodal points, and preferably further comprising at least one preformed support beam 145, preferably at least three preformed support beams 145, which are guided through the at least one hole 147 through the at least one winding assembly 142 to allow subsequent mounting of at least one thin lid 141 at a distance part from the at least one winding assembly 142, preferably forming an air gap with a thickness of at least 0.5 mm between the at least one winding assembly 142 and the at least one lid 141.

FIG. 1I is a block diagram of an example system 190 for magnetic stimulation. The system 190 includes a pulse generator 192 configured to generate a magnetic stimulation pulse, e.g., a pulse appropriate for transcranial magnetic stimulation of a subject 194. The system 190 includes the coil assembly 100 of FIG. 1A, including a winding block, a coil potted in the winding block, and a connector 196 configured to receive the magnetic stimulation pulse and transmit the magnetic stimulation pulse to the coil. A casing encloses the winding block, and the winding block is mounted to the casing at one or more acoustic nodes of the winding block that are subject to a minimum vibration during the magnetic stimulation pulse.

The control system of the pulse generator can be implemented in hardware, software, firmware, or combinations of hardware, software and/or firmware. In some examples, the control systems described in this specification may be implemented using a non-transitory computer readable medium storing computer executable instructions that when executed by one or more processors of a computer cause the computer to perform operations. Computer readable media suitable for implementing the control systems described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application-specific integrated circuits. In addition, a computer readable medium that implements a control system described in this specification may be located on a single device or computing platform or may be distributed across multiple devices or computing platforms.

Figure 2A:
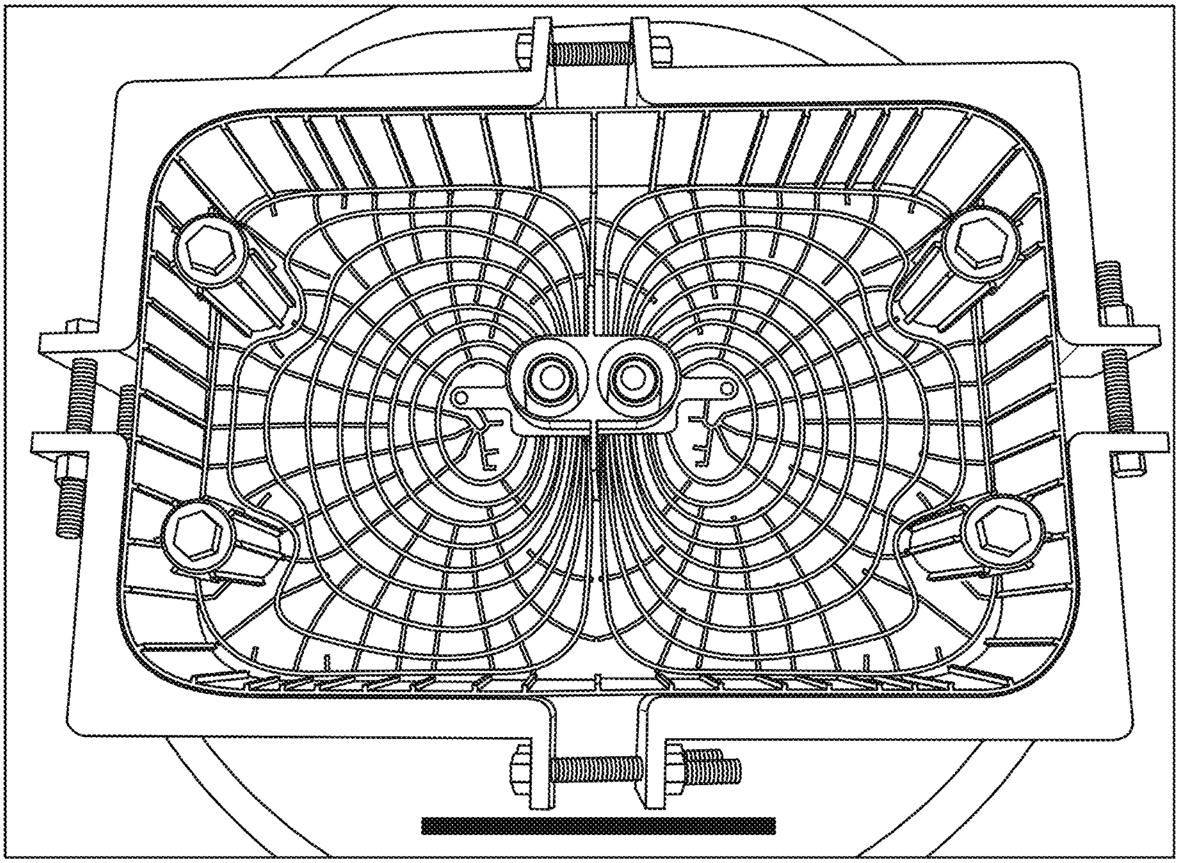
FIGS. 2A-2C show an example coil assembly prototype.
Figure 2B:
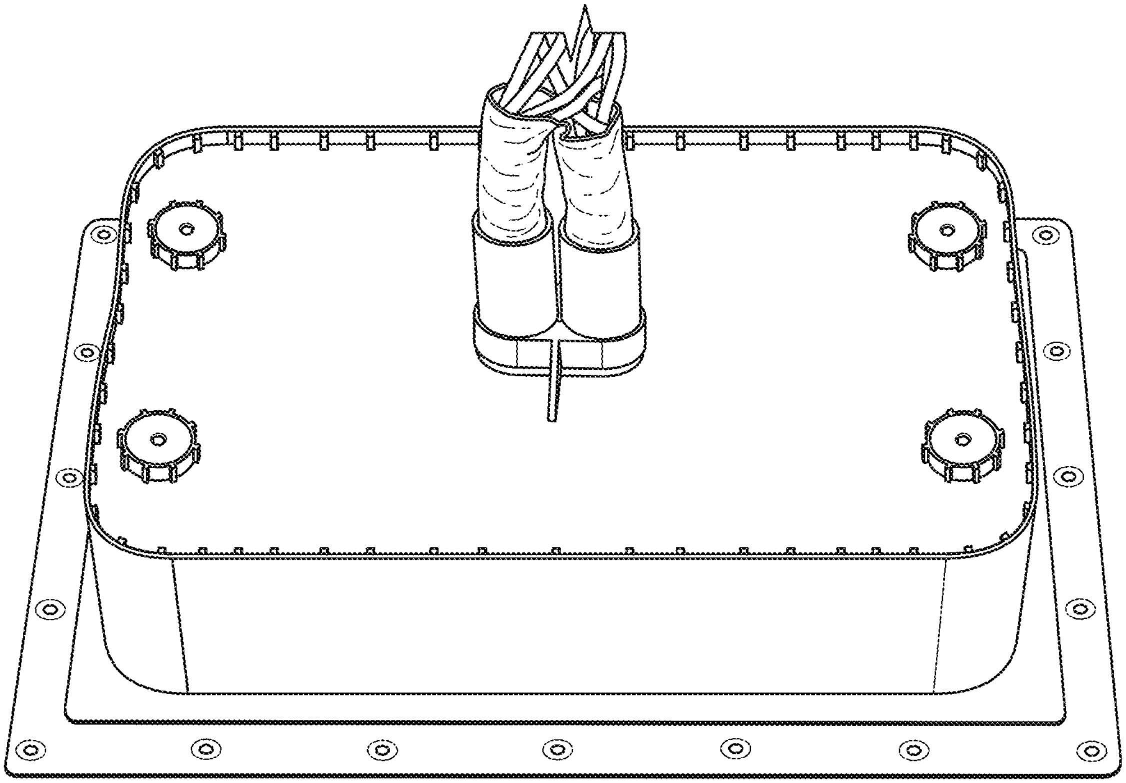
Figure 2C:
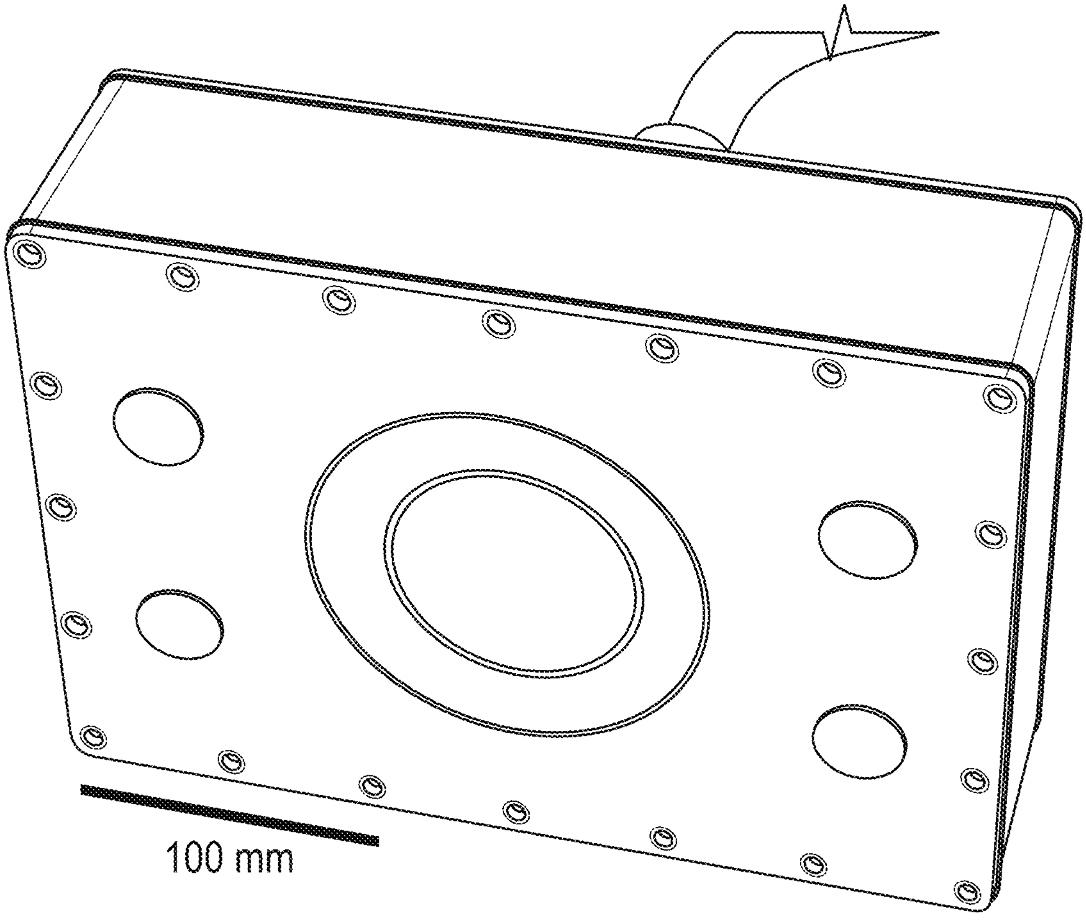

FIGS. 2A-2C show an example coil assembly prototype, called the DCC prototype. The methods and systems described in this document can be implemented using the materials and dimensions described with respect to the DCC prototype or using other appropriate materials and dimensions. The materials used and dimensions described are provided for purposes of illustration and not limitation.

As shown in FIG. 2A, the lid was constructed by laminating a piece of 0.8 mm polyurethane foam between a 0.78 mm FR4 sheet and a 4.76 mm FR4 sheet with polyurethane glue (Gorilla Glue Company, USA). The outer casing was built from another 4.76 mm FR4 sheet and 3d-printed sintered walls from nylon 12 (Xometry, USA). These were connected by bolts, and each interface was sealed with a custom laser-cut butyl rubber gasket.

The coil winding of the prototype was wound from a rectangular solid magnet wire with height of 4.11 mm, width of 1.45 mm, and heavy-build polyimide-enamel insulation (MWS Wire Industries, USA). In some examples, the coil winding can be made using litz wire, which is more efficient for briefer TMS pulses. The winding block was constructed by potting the winding with corundum-filled high-strength lamination epoxy (Fibre Glast, USA) (FIG. 2B). The potting mold was 3d-printed from nylon 12 (Xometry, USA), and had a minimum wall thickness of 0.7 mm and minimum potting thickness of 1.1 mm (FIG. 2A).

Consequently, the bottom of the coil winding was 1.8 mm above the bottom of the winding block, and the total distance between the center of the coil winding and the coil surface was 7.8 mm, which is comparable with commercial TMS coils [33]. The winding was connected to a commercial TMS device (MagPro R30 incl. MagOption, MagVenture, Denmark) with a 3 m low-inductance TMS-coil cable (Magstim, UK) and a customized orange-type SBE 160 power connector (Anderson Power Products/Ideal Industries, USA). The cable exit from the outer casing was sealed with an air-tight cord grip, which was separated from the rest of the outer casing with a butyl rubber gasket. FIG. 2C shows the winding block contained in an outer casing constructed from FR4 sheets and 3d-printed nylon. A circular recession 206 tapering from an outer diameter $D_{outer}$ to an inner diameter $D_{inner}$ is shown in the casing. The scale bar in each of FIGS. 2A-2C is 100 mm long.

Coil Winding Optimization

The optimization problem for the energy efficiency of TMS coil windings is a convex optimization problem [35]. Such problems have a somewhat shallow energy landscape around the optimum. Thus, minor sacrifices in efficiency can lend substantially improved buildability and desired electrical properties such as higher inductance for a given number of turns with lower coil current requirements. This problem can be solved with TMS-coil optimization routines, e.g., further developed from prior work [21]. Specifically, two new types of constraints can be added: a constraint for the magnitude of coil current density and for the maximum dl/dt for the desired E-field in the cortex. The former is a constraint for a norm, solved similarly to the previous E-field norm constraints and satisfied to a tolerance of 0.001. The updated optimization routines were implemented with MATLAB (Global Optimization Toolkit, Version R2018a, Mathworks, USA).

Acoustic Simulations

For acoustic simulation of the coil winding block, we built two models. First, a simple 2d model for the in-plane vibrations was used to tune the optimization constraints for the coil winding. Second, a detailed 3d model was created to estimate the required thickness for the winding block. The latter model was further validated post-hoc against the measurements. For the models, the material parameters for the corundum-filled epoxy were estimated with the S-combining rule [36]. Both models were solved with COMSOL Multiphysics (Version 5.3a, COMSOL, USA).

Electrical Simulations

A TMS coil design has three key electrical parameters: the inductance and resistance of the winding as well as the coupling coefficient to the brain, defined as the ratio between the strength of the E-field induced in the cortex and the rate of change of the coil current. We computed the coupling coefficient for a 85 mm spherical head model with the triangle construction [32], implemented in Mathematica (Version 12.0.0.0, Wolfram Research, USA). The coil inductance and resistance were computed with multipole-accelerated inductance extraction (FastHenry2, Software Bundle 5.2.0, FastFieldSolvers, Italy), and the power cable contribution was modelled with COMSOL.

Acoustic and Electrical Measurements

The acoustic and electrical measurements of the coil were carried out similarly to our previous work characterizing commercial TMS coils [1] with a few minor differences. Notably, we omitted the use of a soundproof chamber and measured the sound in a regular TMS treatment room with the coil facing towards the ceiling, suspended ~20 cm above a 15 cm thick open-cell foam panel and all walls at least 2 m from the coil to avoid early reflections. Further, we averaged 9 TMS pulses per condition to suppress the effects of the ambient noise.

Figure 4:
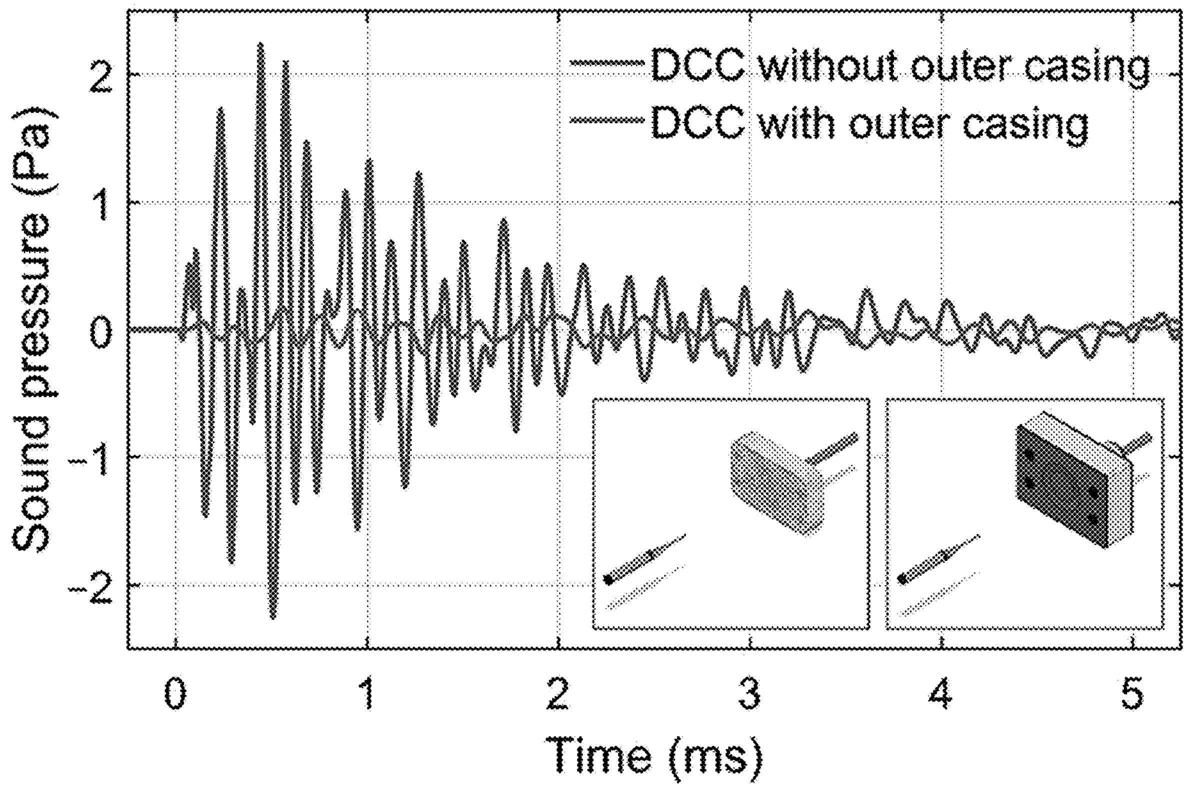
FIG. 4 shows sound pressure waveforms from the DCC prototype and its winding block.

Briefly, for acoustic measurements, an omnidirectional flat-frequency-response pressure microphone (M50, Earthworks Audio, USA) was placed 25 cm from the center of the head-facing side of the coil (FIG. 4, inset). The microphone output was fed to a wide-input-signal-range preamplifier (RNP8380, FMR Audio, USA) and then an audio interface with a sample rate of 192 KHz (U-Phoria UMC404HD, Behringer, Germany). The measurement system was calibrated with a 1 kHz, 1 Pa reference sound pressure source (407722, Extech Instruments, USA). We recorded the sound from single TMS pulses at 10% to 100% of maximum stimulator output (MSO) in 10% MSO increments. The continuous sound of rTMS was synthesized from these pulses. To extract the SPL and SL, the audio was processed with the MATLAB Audio Toolbox. We used the electromagnetic artefact removal algorithm as well as low- and high-pass filters described in our previous study [1].

The measurement distance, 25 cm, was chosen to avoid inadequate spatial sampling of the sound in the near field and allow filtering out the electromagnetic artefact from the stimulation [1]. As the sound of TMS attenuates approximately inversely with distance down to about 5 cm [40], we estimated the SPL and SL at the subject's ears, 5 cm from the coil, by adding 14 dB to the measurements at 25 cm [1]. As the DCC is larger than typical TMS coils, we validated this extrapolation approach with laser Doppler vibrometer (LDV) measurements (see Supplementary material).

The induced E-field was measured with a printed-circuit-board-based triangular probe [1] connected to an oscilloscope (DS1052E, Rigol, China) with a sampling rate of 250 MHz. To estimate the effective neural stimulation strength, the recorded waveform was fed into a strength-duration model [41], with a time constant of 200 μs. Additionally, we recorded the maximum rate of change for the coil current from the sensor built into the TMS device. The stimulation strength was calibrated to the average measured resting motor threshold (RMT) of normal subjects extracted from the literature [1].

Finally, to validate our acoustic simulation model and to identify the resonant modes present in our winding block and DCC, we performed non-contact measurement of surface vibrations with an LDV (PSV-400, Polytec, Germany). As both 3d-printed nylon and FR4 scatter the laser, we built small markers from 0.1 mm thick retroreflective vinyl tape. The winding block bottom was sampled with a 5×5 grid, and the DCC lid with 41 points on a sparse 13×7 grid. In addition, we sampled 4 points from the short and long sides of the winding block and the outer casing (including 1 point on the power connector), and 4 points from the power cable at the coil end with a 5 cm spacing.

Results

Coil Winding and Construction

The acoustic simulations of the in-plane vibrations of the winding gave up to four nodal points of greatly reduced mechanical vibrations. The locations of these points depend mostly on the coil size, and to lesser extent on Poisson's ratio of the potting material. For epoxy-like materials (Poisson's ratio about 0.3), four nodal points were identified in the corners of a 180 mm×130 mm winding block. To move these points away from the corners and place them along the nodal line for the short-edge resonant mode of the winding block, we chose to implement a slightly larger, 225 mm×145 mm winding block. To obtain adequate stiffness and sufficiently high resonant frequencies for the out-of-plane vibration modes, the out-of-plane vibration model suggested winding block thickness of at least 40 mm; therefore, we aimed for a thickness of 45 mm. We designed the winding to match the E-field focality of a Magstim 70 mm Double Coil in the 85 mm spherical head model. The resulting winding is shown in FIG. 2A.

For the potting material, we chose the highest attainable total epoxy-to-corundum mass mixing ratio, 1:3.5 (49.4% corundum by volume). We prepared a small batch with mass mixing ratio of 1:2 (35.6% by volume), which is the highest fill ratio with adequate fluidity to flow around the winding, and a large batch with mixing ratio of 1:4 (52.5% by volume), which corresponds to a self-leveling thick paste. Both batches were de-aired in a vacuum desiccator. The two-stage potting process consisted of covering the winding with the small batch, removing any trapped air under the winding with a vacuum desiccator, and filling the rest of the mold with the large batch. The realized thickness of the potting was 47 mm. To maximize the epoxy strength, the potted winding block was post-cured at 85° C. for three hours.

Electrical Properties

The simulated coil inductance and resistance were, respectively, 11.1 μH (10.9 pH for the coil winding and 0.15 μH for the power cable) and 19.6 mΩ (14.3 mΩ for the winding and 5.3 mΩ for the cable) at 3.3 kHz. At 1 KHz, the coil resistance dropped to 18.3 mΩ, and at 10 KHz it rose to 25.9 mΩ. These values matched very well the respective measurements of 11.9 μH and 22.2 mΩ at 1 KHz, and 11.8 pH and 33.3 mΩ at 10 KHz, acquired with B&K Precision Model 889A Bench LCR/ESR Meter (B&K Precision Corporation, USA). The unaccounted inductance and resistance likely stem from parasitic inductance and resistance associated with the connections between the winding, coil cable, and measurement probe.

The simulated coupling coefficient to cortex was 1.42 (V/m)/(A/μs) for the entire coil, and 1.67 (V/m)/(A/μs) for the exposed coil winding block. When connected to the MagPro TMS device, the pulse duration for biphasic TMS pulses was 298 μs, which was close to conventional MagVenture coils. The measured coupling coefficients were 1.42 (V/m)/(A/μs) for the coil, and 1.67 (V/m)/(A/μs) for the exposed winding block, matching the simulations. Thus, the outer casing reduced the E-field magnitude and the associated stimulation strength by 15%. Consequently, the stimulation strength at 100% MSO was 275% and 323% of average RMT for the entire coil and the exposed winding block, respectively.

Acoustic Properties

The SL of the ambient noise in our TMS treatment room was 45 dB (A), and the peak SPL in the 0.2 s measurement window was 71 dB (Z), both about 25 dB above the ambient noise in our earlier measurements inside a soundproof chamber [1]. Given the reduction of SL and SPL for the DCC compared to commercial TMS coils, the ambient noise prevented measuring the sound from subthreshold pulses but was low enough to have negligible effect on the sound recordings near the maximum stimulator output. In addition to the elevated noise background, we further identified a few narrowband ultrasonic sound sources, at 25.0 kHz, 45.1 kHz, and 51.5 kHz, likely from presence of sensors for the room lighting and air conditioning. The strongest of these three sources was at 25.0 kHz and had ⅓-octave sound level of 35 dB. The averaging suppressed these artefacts and had negligible effect (<0.1 dB) on both SL and SPL at maximum stimulator output, which confirms that it did not reduce the TMS sound.

As the coil sound scales similarly to other air-core TMS coils, we report numbers only for a stimulation strength of 120% RMT for a subject with a top 5 percentile RMT, i.e., about 167% of average RMT [1]. For rTMS, we used the highest repetition rate sustained for several seconds in clinical treatments, 20 Hz [43], [44]. The numbers can be scaled to other stimulation strengths and repetition rates as described in [1].

Figure 3:
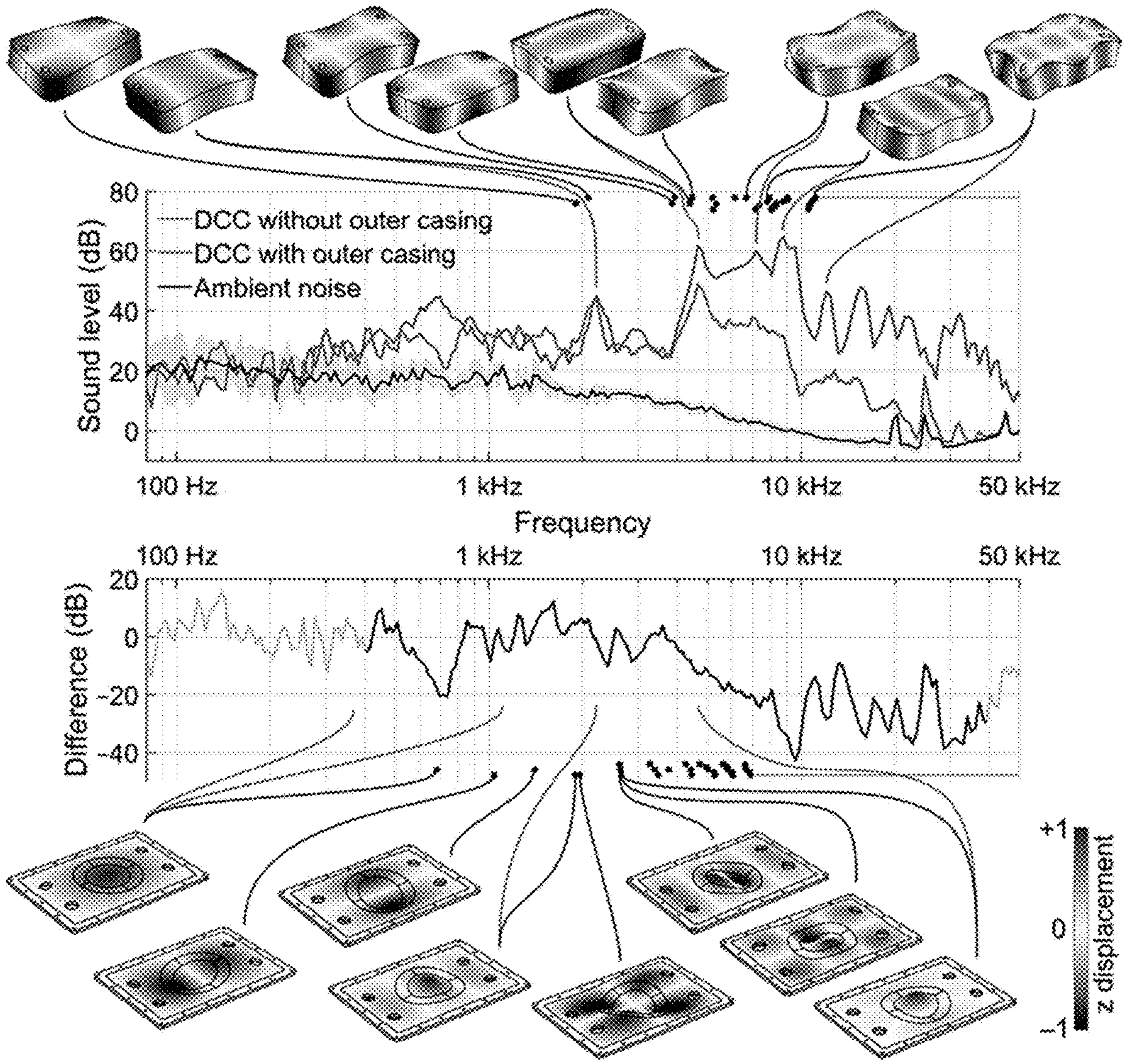
FIG. 3 illustrates sound spectra and mechanical vibration modes of the prototype DCC.

FIG. 3 illustrates sound spectra and mechanical vibration modes of the prototype DCC. The measured sound spectra plots in dB are compared with the simulated mechanical modes (illustrated with surface displacement plots, black dots denoting the resonant frequencies, and black lines connecting them) as well as the LDV measured modes.

The top frame shows winding block vibration modes. The second row shows 1/24-octave sound level of the winding block and complete coil with outer casing at 167% average resting motor threshold (RMT). To reduce the ambient noise level, 9 pulses were averaged for each trace. The gray band denotes the 95% confidence interval of the averaged ambient noise measurement. The third row shows attenuation provided by the outer casing obtained by subtracting the winding block spectrum from the complete coil spectrum. Despite averaging, the attenuation spectrum at frequencies below 400 Hz and above 40,000 Hz could not be measured reliably and is therefore grayed out.

The bottom row shows vibration modes of the outer casing lid. All four LDV measured resonant peaks are likely driven by the winding block motion: the two frequencies at which the lowest mode is active correspond to frequencies at which there is solid motion of the winding block, likely driven by the power cable and coil connector vibration, and the two higher modes are at the exact frequencies of the long and short modes of the winding block, respectively.

FIG. 4 shows sound pressure waveforms from the DCC prototype and its winding block. In both cases, the microphone was centered 25 cm from the closest head-facing surface (insets). The start of the TMS pulses is at −0.73 ms to compensate for the sound propagation delay in the air. The exposed winding block (101 dB (Z) peak) is compared to the complete coil with outer casing (79 dB (Z) peak). Both configurations are measured for stimulation strength of 167% RMT; thus, the complete coil had 18% higher current to compensate for the thickness of the casing.

Figure 5:
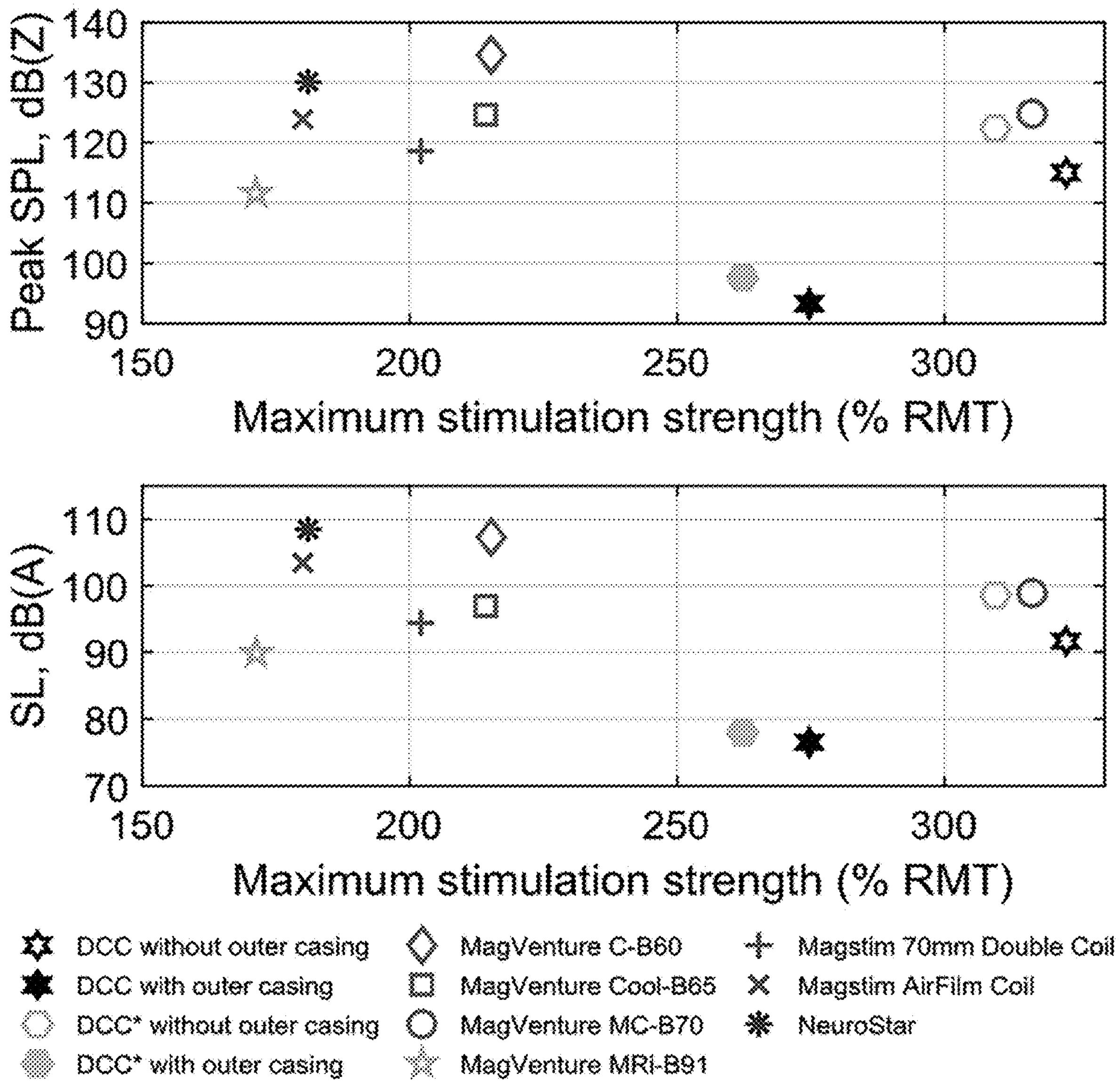
FIG. 5 shows measured TMS coil sound levels as a function of the stimulation strength obtained at maximum stimulator output.

FIG. 5 shows measured TMS coil sound levels as a function of the stimulation strength obtained at maximum stimulator output. The peak SPL (top) and SL of 20 Hz rTMS (bottom) were measured at 25 cm from the coils at 167% average RMT and extrapolated to 5 cm distance by adding 14 dB. Apart from the DCC measurements, the commercial coil data are reproduced from our prior work [1]. DCC* is a litz-wire version of DCC intended primarily for high-voltage ultra-brief TMS pulses.

For the coil winding block, the peak SPL at 167% RMT was 101 dB (Z). With the outer casing, the peak SPL was reduced by 22 dB (Z) to 79 dB (Z) (see FIG. 4). The peak SPL was 18 dB (Z) lower than the quietest coil in our database [1], which is a commercial MRI-compatible coil (MagVenture MRi-B91); 25 dB (Z) lower than the quietest conventional TMS coil; 32 dB (Z) lower than the only coil with a comparable maximum stimulation strength, which has an angled winding topology; and 41 dB (Z) lower than the loudest coil (FIG. 5, top).

The continuous SL of a 20 Hz rTMS train, for the coil winding block, was 78 dB (A). With the outer casing this level was reduced by 15 dB (A) to 63 dB (A). This was 13 dB (A) lower than the commercial MRI-compatible coil, 18 dB (A) lower than the best conventional coil, 22 dB (A) lower than the only coil with comparable maximum stimulation strength, and 32 dB (A) lower than the loudest coil (FIG. 5, bottom).

The 1/24-octave sound spectrums (FIG. 3, second row) indicate that the winding block emits most of its sound in a broad peak around 7 kHz, i.e., at twice the TMS pulse frequency of 3.35 kHz. This is expected for normal TMS coils, as the mechanical vibrations are driven by the Lorentz forces which are proportional to the squared coil current, and hence have their spectral power peak at double the current frequency. The LDV measurement of the winding block bottom showed five resonant peaks that matched their simulated counterparts: 2.2, 4.7, 7.2, 8.8, and 12.0 KHz (FIG. 3, top).

For the DCC lid, we observed four resonant peaks: 0.4, 1.1, 2.2, and 4.8 kHz (FIG. 3, bottom). The LDV data further explains the peak at 0.6 kHz, which originates from the vibrations of the coil power connector visible in FIG. 2B. The outer casing attenuates frequencies above 4 kHz (FIG. 3, third row), with typical attenuation above 8 kHz of approximately 30 dB. With the outer casing, there is a minimal amount of near-ultrasound content. Thus, the outer casing of the coil acts as an acoustic low-pass filter (FIG. 3, bottom).

DISCUSSION

The methods and systems described in this document can reduce the sound of TMS compared to some conventional TMS systems. The double-containment coil design maximized the mismatch in acoustic impedance in the path between the winding and the casing without significantly increasing the thickness of the acoustic containment structure. The sound containment provides superior acoustic insulation compared to a layer of acoustic foam that is approximately twice as thick in commercial MRI-compatible TMS coils, which are relatively quiet but have reduced maximum stimulation strength. The DCC further utilized a winding that was optimized for maximal energy efficiency despite the additional thickness of the casing. This resulted in a coil that, with the same TMS device, has both higher maximum stimulation strength and lower acoustic emissions than any conventional flat figure-8 coil we tested.

We measured the sound levels at 25 cm and extrapolated sound levels to 5 cm to match the typical distance to the subject's ears. The extrapolated values are approximate, as they approximated the coil as a point source and were computed simply by multiplying the measured sound waveform by 5, which scales up the spectrum at all frequencies by 14 dB. Since the coil is not a point source but a distributed sound pressure source, the extrapolation may overestimate some components especially in the high frequencies (beyond 10 kHz). Further, as the low frequencies have wavelength comparable to the measurement distance, the extrapolation may underestimate some components at low frequencies (up to about 3 kHz). As this extrapolation assumes a point source, it can be less accurate for some larger coils. Based on our supplementary LDV data, for the DCC and its winding block in particular, the extrapolation is reasonably accurate for distances down to about 3 cm.

Some aspects of the DCC prototype were designed based on qualitative considerations and approximations for the coil design necessary for our quiet TMS framework, which aims to use high-amplitude ultra-brief pulses [34]. Consequently, the design was optimized to accommodate windings made of litz wire with higher voltage insulation. Moreover, since the pulse amplitude required for stimulation with ultra-brief pulses is presently uncertain, the coil design aimed for a high maximum E-field output instead of matching the output to conventional coils, which would let us minimize the sound further.

For example, to maximize the coil stimulation efficiency, we chose to implement a moderately thin combination of air gap and lid (4.0 mm). Should this high output not be needed, the sound attenuation by the outer casing can be improved by increasing either the width of the air gap (which reduces the duration of the sound reverberation inside the outer containment) or the thickness of the window in the lid (which further reduces the sound transmission). Alternatively, for the implementation with rectangular solid magnet wire, the coil winding can be redesigned to use a taller, and thus heavier, wire. This will increase the density and stiffness of the winding block, and thus reduce the emitted sound. The optimum values for the three variables depend on both the lid and wire materials and the desired maximum stimulation strength.

Further Examples

The DCC design described above can be modified to include two design changes for improved operation in some cases. The first one is the new design elements of our compact double-containment coil (cDCC) for quiet transcranial magnetic stimulation (TMS). The cDCC has been designed to have size comparable to large, conventional TMS coils, to have electromagnetic characteristics of a 'standard' figure-of-eight type TMS coil, and, crucially, to retain superior acoustic performance when compared to any conventional TMS coils. And, the second one is experimental validation of tunable acoustic performance of the original DCC winding block. By increasing the air-gap, and by moving the coil mounting to happen from the backplate of the outer casing instead of its lid, we have further reduced the sound. The internal structure of the cDCC is largely similar to the DCC, described above. In short, the coil comprises:

1. A winding block, suspended inside an outer casing; and
2. The outer casing.

The connection between the winding block and the outer casing is what we call minimally rigid. That is, the winding block is only connected to the outer casing from its acoustic nodes. That is, from areas subject to least vibration due to TMS pulses. The connection is further made with flexible connectors. For the DCC, there were four nodes near the perimeter. For cDCC, there are two nodes near the center.

Figure 6:
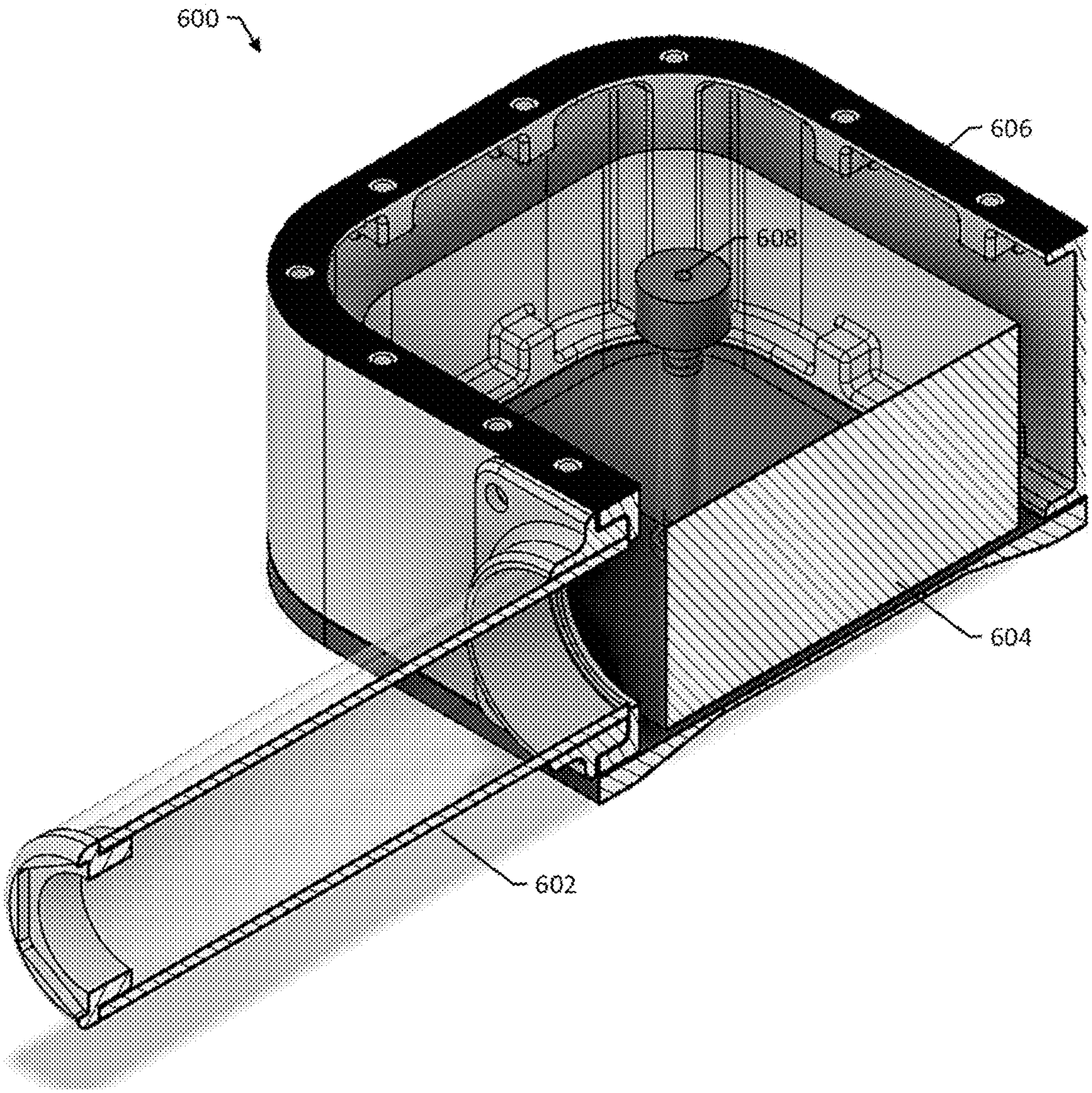
FIG. 6 shows a 3d model of the cDCC.

FIG. 6 shows a 3d model of the cDCC 600. The power cable enters the coil from bottom left corner, through the hollow handle 602. The winding block 604 (pictured with a transparent cuboid with rounded edges) is suspended inside the outer casing 606 from the acoustic nodes (e.g., acoustic node 608) of the winding block 604. For this smaller winding block 604, there are two acoustic nodes, and consequently, at least one of these two nodes need to attach to the winding block 604 at two different heights to fully constraint the motion and rotation of the winding block 604 with respect to the outer casing 606. The winding block 604 is suspended with four rubber o-rings (two for each node, one near the bottom and one near the top), which are held in place by the cylindrical shafts mounted to the lid and the backplate of the outer casing 606.

Figure 7:
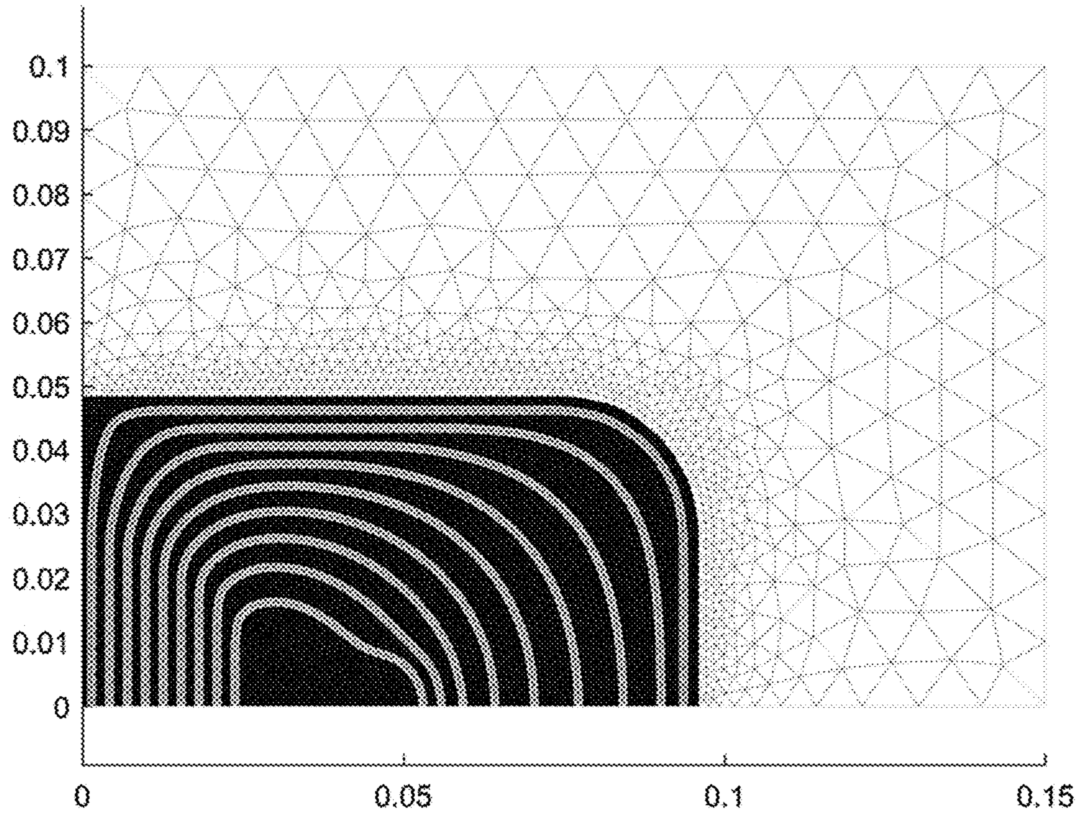
FIG. 7 shows one quadrant of the coil winding inside the winding block.
Figure 8:
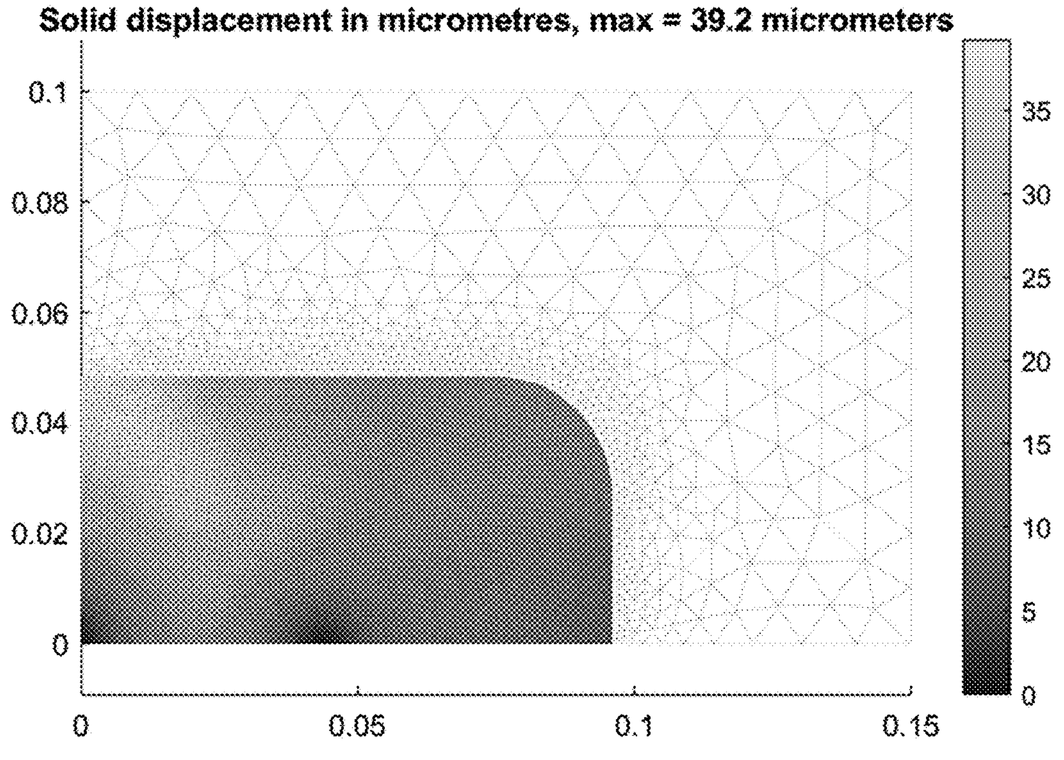
FIG. 8 shows an estimate of the amplitude of mechanical vibrations for different parts of the winding block.

FIG. 7 shows one quadrant of the coil winding inside the winding block. The winding has been designed to facilitate an acoustic node at (±45 mm, 0). FIG. 8 shows an estimate of the amplitude of mechanical vibrations for different parts of the winding block. The two nodes are at (±0.045 m, 0), a location which the winding shown in FIG. 7 does not have a wire to allow for the mounting solution.

Figure 9:
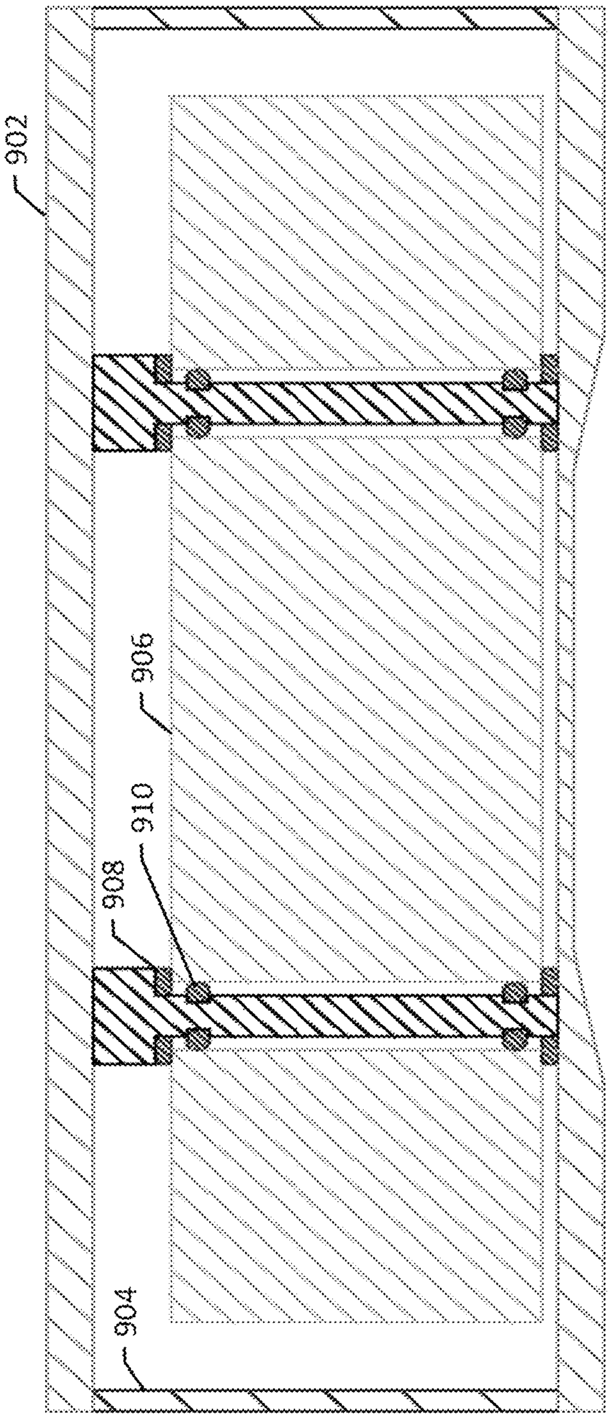
FIG. 9 shows a cross-section of the winding-block mount.

FIG. 9 shows a cross-section of the winding-block mount. The outer lighter parts 902 are the FR4 lid and the backplate, the darker outer parts 904 are the nylon walls. These form the outer casing. (The outer casing may be made of any solid, non-conductive material, and the seams in it have no functional purpose. That is, it can also be made from one material.)

The inner lighter part is the winding block 906. It is suspended between two rubber washers (e.g., washer 908) on each of the mounting points and its lateral movement and rotation are constrained by two rubber o-rings (e.g., o-ring 910) at each mounting point. The rubber parts connect the winding block to two cylindrical members that are rigidly mounted to the outer casing. The key aspect of this mounting solution is the limited area of the winding block that it covers, so that the winding is only connected to the coil exterior from areas of least vibration. Like with DCC, for cDCC, but not depicted in this cross-section, the cavity between the winding block and the outer casing is mostly or at least partially filled with sound absorbing material. This reduces the duration of reverb of the coil sound.

The design changes to the internal structure of the DCC can include:

1. Mounting from the back of the winding block with mounts somewhat similar to FIG. 9 (except that they do not touch the lid)
2. Taller walls for the outer casing to move the lid further
3. Adding vibration damping rubber sheet to the interior surface of the lid Electromagnetic Characterization On a benchtop characterization, the cDCC coil (including the power cable and connector) has an inductance of 11.10 μH at 1 KHz and 10.88 μH at 10 KHz and a resistance of 26.2 mohm and 39.5 mohm, respectively. The inductance value can be tuned, and indeed for cDCC, we could have reached the same inductance with three different number of turns (with less turns, we lose some efficiency but also reduce the resistive losses). We chose the intermediate one for this prototype, for no particular reason as all three solutions appeared reasonable on simulations.

Connected to a MagVenture MagPro X100 incl. MagOption-device, the coil closely resembles the 'standard-size' figure-of-eight coil. The pulse duration is similar but slightly shorter at 280 μs due to slightly lower inductance (about 11 μH instead of about 12 μH). Most importantly, however, the stimulation strength at any given 'amplitude' setting on the device is almost perfectly matched to coil such as MagVenture Cool-B65. This is different from DCC, which was more efficient and thus produced stronger stimulation at matched settings. For cDCC, we sacrificed the efficiency advantage to reduce the coil size. At 100% MSO, the cDCC provides a stimulation strength of 215% RMT.

For the thicker DCC, the inductance and resistance are unchanged, as is the pulse waveform. The pulse amplitude is reduced by the increased airgap so that the maximum stimulation strength is 220% RMT.

Acoustic Performance

As expected, the cDCC loses some performance compared to DCC, especially for peak SPL. This is due to several reasons, including cDCC requiring more power for same stimulation, and the lighter winding block in the cDCC vibrating more for given impulse. Compared to commercial coils, cDCC is, however, still much quieter than any commercial coil we have tested.

The proportionally better performance for SL compared to SPL is due to further reduction of low frequency 'rumble' of the outer casing. This is a side benefit of making the coil smaller.

The thick DCC reduces both peak SPL and SL. This is due to very good suppression of the early component of TMS sound, which removes most of the high-frequency content of the coil click.

SUMMARY

The cDCC is a more compact version of DCC. Further, we have designed the cDCC to match the electromagnetic performance of commercial TMS coils, rather than exceeding that. This allowed us to reduce the size of the internal components within the cDCC. In total, these two allowed us to reduce the size of the coil to resemble large conventional coils, whilst still offering acoustic performance greatly exceeding that of conventional coils.

CONCLUSION

The DCC, DCC*, and cDCC coil designs substantially reduce the instantaneous peak sound pressure level and the continuous sound level during TMS, while providing higher maximum stimulation strength. This can mitigate problems associated with the TMS coil sound.

Accordingly, while the methods and systems have been described herein in reference to specific embodiments, features, and illustrative embodiments, it will be appreciated that the utility of the subject matter is not thus limited, but rather extends to and encompasses numerous other variations, modifications and alternative embodiments, as will suggest themselves to those of ordinary skill in the field of the present subject matter, based on the disclosure herein.

Various combinations and sub-combinations of the structures and features described herein are contemplated and will be apparent to a skilled person having knowledge of this disclosure. Any of the various features and elements as disclosed herein may be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims.

REFERENCES

[1] L. M. Koponen et al., "Sound comparison of seven TMS coils at matched stimulation strength," *Brain Stimulat.*, vol. 13, no. 3, pp. 873-880, May 2020, doi: 10.1016/j.brs.2020.03.004.

[2] *ANSI/ASA S*1.4-2014*/Part* 1. *American National Standard Electroacoustics—Sound Level Meters—Part* 1*: Specifications* (*a nationally adopted international standard*). Melville, NY: Acoustical Society of America, 2014.

[3] S. Rossi et al., "Safety, ethical considerations, and application guidelines for the use of transcranial magnetic stimulation in clinical practice and research," *Clin. Neurophysiol., vol.* 120, no. 12, pp. 2008-239 December 2009, doi: 10.1016/j.clinph.2009.08.016.

[4] S. M. Goetz et al., "Impulse noise of transcranial magnetic stimulation: measurement, safety, and auditory neuromodulation," *Brain Stimulat.*, vol. 8, no. 1, pp. 161-163, January 2015, doi: 10.1016/j.brs.2014.10.010.

[5] R. L. Folmer and S. M. Theodoroff, "Hearing protective devices should be used by recipients of repetitive transcranial magnetic stimulation," *J. Clin. Neurophysiol.*, vol. 34, no. 6, p. 552, November 2017, doi: 10.1097/WNP.0000000000000413.

[6] A. Zangen et al., "Transcranial magnetic stimulation of deep brain regions: evidence for efficacy of the H-coil," *Clin. Neurophysiol.*, vol. 116, no. 4, pp. 775-779, April 2005, doi: 10.1016/j.clinph.2004.11.008.

[7] P. R. Martin et al., "Noise as a trigger for headaches: relationship between exposure and sensitivity," *Headache J. Head Face Pain*, vol. 46, no. 6, pp. 962-972, May 2006, doi: 10.1111/j.1526-4610.2006.00468.x.

[8] C. Wöber et al., "Trigger factors of migraine and tension-type headache: experience and knowledge of the patients," *J. Headache Pain*, vol. 7, no. 4, pp. 188-195, September 2006, doi: 10.1007/s10194-006-0305-3.

[9] V. Nikouline et al., "The role of the coil click in TMS assessed with simultaneous EEG," *Clin. Neurophysiol.*, vol. 110, no. 8, pp. 1325-1328 August 1999, doi: 10.1016/S1388-2457 (99) 00070-X.

[10] S. Bestmann et al., "BOLD MRI responses to repetitive TMS over human dorsal premotor cortex," *NeuroImage*, vol. 28, no. 1, pp. 22-29, October 2005, doi: 10.1016/j.neuroimage.2005.05.027.

[11] W. C. Clapp et al., "Induction of LTP in the human auditory cortex by sensory stimulation," *Eur. J. Neurosci.*, vol. 22, no. 5, pp. 1135-1140 September 2005, doi: 10.1111/j.1460-9568.2005.04293.x.

[12] T. Zaehle et al., "Induction of LTP-like changes in human auditory cortex by rapid auditory stimulation: an fMRI study," *Restor. Neurol. Neurosci.*, vol. 25, no. 3/4, pp. 251-259, May 2007.

[13] S. P. Schraven et al., "Hearing safety of long-term treatment with theta burst stimulation," *Brain Stimulat.*, vol. 6, no. 4, pp. 563-568, July 2013, doi: 10.1016/j.brs.2012.10.005.

[14] S. N. Kukke et al., "Hearing safety from single- and double-pulse transcranial magnetic stimulation in children and young adults," *J. Clin. Neurophysiol., vol.* 34, no. 4, pp. 340-347, July 2017, doi: 10.1097/WNP.0000000000000372.

[15] E. H. Berger, "Methods of measuring the attenuation of hearing protection devices," *J. Acoust. Soc. Am.*, vol. 79, no. 6, pp. 1655-1687 June 1986, doi: 10.1121/1.393228.

[16] M. Toivonen et al., "Noise attenuation and proper insertion of earplugs into ear canals," *Ann. Occup. Hyg.*, vol. 46, no. 6, pp. 527-530, July 2002, doi: 10.1093/annhyg/mef065.

[17] R. Neitzel et al., "Variability of real-world hearing protector attenuation measurements," *Ann. Occup. Hyg.*, vol. 50, no. 7, pp. 679-691, October 2006, doi: 10.1093/annhyg/mel025.

[18] A. M. Smith, "Real-world attenuation of foam earplugs," *Aviat. Space Environ. Med.*, vol. 81, no. 7, pp. 696-697, July 2010, doi: 10.3357/ASEM.2817.2010.

[19] H. Nélisse et al., "Measurement of hearing protection devices performance in the workplace during full-shift working operations," *Ann. Occup. Hyg.*, vol. 56, no. 2, pp. 221-232, March 2012, doi: 10.1093/annhyg/mer087.

[20] M. Massimini et al., "Breakdown of cortical effective connectivity during sleep," *Science*, vol. 309, no. 5744, Art. no. 5744 September 2005, doi: 10.1126/science.1117256.

[21] L. M. Koponen et al., "Coil optimisation for transcranial magnetic stimulation in realistic head geometry," *Brain Stimulat.*, vol. 10, no. 4, pp. 795-805, July 2017, doi: 10.1016/j.brs.2017.04.001.

[22] H.-S. Vu and K.-H. Chen, "A low-power broad-bandwidth noise cancellation VLSI circuit design for in-ear headphones," *IEEE Trans. Very Large Scale Integr. VLSI Syst.*, vol. 24, no. 6, pp. 2013-225 June 2016, doi: 10.1109/TVLSI.2015.2480425.

[23] H.-S. Vu and K.-H. Chen, "Corrections to 'A low-power broad-bandwidth noise cancellation VLSI circuit design for in-ear headphones' [2015 DOI: 10.1109/TVLSI.2015.2480425]," *IEEE Trans. Very Large Scale Integr. VLSI Syst.*, vol. 24, no. 6, pp. 2412-2412 June 2016, doi: 10.1109/TVLSI.2016.2544342.

[24] C. Liu et al., "Noise analysis and active noise control strategy of transcranial magnetic stimulation device," *AIP Adv.*, vol. 9, no. 8, p. 085010, August 2019, doi: 10.1063/1.5115522.

[25] T. Paus et al., "Synchronization of neuronal activity in the human primary motor cortex by transcranial magnetic stimulation: an EEG study," *J. Neurophysiol.*, vol. 86, no. 4, pp. 1983-1990 October 2001, doi: 10.1152/jn.2001.86.4.1983.

[26] E. M. ter Braack et al., "Masking the auditory evoked potential in TMS-EEG: a comparison of various methods," *Brain Topogr.*, vol. 28, no. 3, pp. 520-528, May 2015, doi: 10.1007/s10548-013-0312-z.
[27] S. J. Schlittmeier et al., "The impact of road traffic noise on cognitive performance in attention-based tasks depends on noise level even within moderate-level ranges," *Noise Health*, vol. 17, no. 76, pp. 148-157, April 2015, doi: 10.4103/1463-1741.155845.
[28] *American Conference of Governmental Industrial Hygienists, Threshold Limit Values and Biological Exposure Indices*. Cincinnati, OH: ACGIH, 2012.
[29] MIL-STD-1474E. *Department of Defense design criteria standard noise limits*. Washington, DC: AMSC 9542, 2015.
[30] *Recommended Practices for Safety and Health Programs*. Washington, DC, USA: Occupational Safety and Health Administration, 2016.
[31] R. Ilmoniemi et al., "Stimulator head and method for attenuating the sound emitted by a stimulator coil," U.S. Pat. No. 6,503,187B1, Jan. 7, 2003.
[32] J. O. Nieminen et al., "Experimental characterization of the electric field distribution induced by TMS devices," *Brain Stimulat.*, vol. 8, no. 3, pp. 582-589, May 2015, doi: 10.1016/j.brs.2015.01.004.
[33] S. M. Goetz et al., "Transcranial magnetic stimulation device with reduced acoustic noise," *IEEE Magn. Lett.*, vol. 5, pp. 1-4, August 2014, doi: 10.1109/LMAG.2014.2351776.
[34] A. V. Peterchev et al., "Quiet transcranial magnetic stimulation: status and future directions," in 2015 37*th Annual International Conference of the IEEE Engineering in Medicine and Biology Society* (*EMBC*), August 2015, pp. 226-229, doi: 10.1109/EMBC.2015.7318341.
[35] L. M. Koponen et al., "Minimum-energy coils for transcranial magnetic stimulation: application to focal stimulation," *Brain Stimulat.*, vol. 8, no. 1, pp. 124-134, January 2015, doi: 10.1016/j.brs.2014.10.002.
[36] S. McGee and R. L. McGullough, "Combining rules for predicting the thermoelastic properties of particulate filled polymers, polymers, polyblends, and foams," *Polym. Compos.*, vol. 2, no. 4, pp. 149-161, October 1981, doi: 10.1002/pc.750020403.
[37] Z.-D. Deng et al., "Electric field depth-focality tradeoff in transcranial magnetic stimulation: Simulation comparison of 50 coil designs," *Brain Stimulat.*, vol. 6, no. 1, pp. 1-13, January 2013, doi: 10.1016/j.brs.2012.02.005.
[38] R. J. Ilmoniemi, "The triangle phantom in magnetoencephalography," *J. Jpn. Biomagn. Bioelectromagn. Soc.*, vol. 22, no. 1, pp. 44-45, May 2009.
[39] M. Kamon et al., "FASTHENRY: a multipole-accelerated 3-D inductance extraction program," *IEEE Trans. Microw. Theory Tech.*, vol. 42, no. 9, pp. 1750-1758 September 1994, doi: 10.1109/22.310584.
[40] J. Starck et al., "The noise level in magnetic stimulation," *Scand. Audiol.*, vol. 25, no. 4, pp. 223-226, January 1996, doi: 10.3109/01050399609074958.
[41] A. T. Barker et al., "Magnetic nerve stimulation: the effect of waveform on efficiency, determination of neural membrane time constants and the measurement of stimulator output.," *Electroencephalogr. Clin. Neurophysiol. Suppl.*, vol. 43, pp. 227-237, 1991.
[42] A. V. Peterchev et al., "Pulse width dependence of motor threshold and input-output curve characterized with controllable pulse parameter transcranial magnetic stimulation," *Clin. Neurophysiol.*, vol. 124, no. 7, pp. 1364-1372 July 2013, doi: 10.1016/j.clinph.2013.01.011.
[43] V. Desbeaumes Jodoin et al., "Safety and efficacy of accelerated repetitive transcranial magnetic stimulation protocol in elderly depressed unipolar and bipolar patients," *Am. J. Geriatr. Psychiatry*, vol. 27, no. 5, pp. 548-558, May 2019, doi: 10.1016/j.jagp.2018.10.019.
[44] J.-P. Miron et al., "Safety, tolerability and effectiveness of a novel 20 Hz rTMS protocol targeting dorsomedial prefrontal cortex in major depression: an open-label case series," *Brain Stimulat.*, vol. 12, no. 5, pp. 1319-1321 September 2019, doi: 10.1016/j.brs.2019.06.020.

What is claimed is:

1. A coil assembly for transcranial magnetic stimulation, the coil assembly comprising: a winding block; a coil in the winding block; and a casing enclosing the winding block, wherein the winding block is mounted to the casing at two or more acoustic nodes of the winding block that are subject to a minimal vibration during a transcranial magnetic stimulation pulse, and wherein the winding block is mounted to the casing by one or more rubber grommets and nylon bolts at the respective acoustic node, wherein each of the acoustic nodes is identified as point in the winding block having minimal amplitude of vibrations while the coil is mechanically excited during the magnetic stimulation pulse.

2. The coil assembly of claim 1, wherein an air cavity separates the winding block from the casing outside of the one or more acoustic nodes.

3. The coil assembly of claim 2, wherein the air cavity is at least partially filled with an acoustic foam.

4. The coil assembly of claim 1, wherein the casing comprises one or more sound absorbing panels.

5. The coil assembly of claim 1, wherein the casing comprises a recession under a winding center of the coil, and wherein a casing thickness of the casing is thinner within the recession than it is in at least one other region outside of the recession.

6. The coil assembly of claim 5, wherein the recession comprises a circular recession tapering from an outer diameter of the circular recession to an inner diameter of the circular recession.

7. The coil assembly of claim 1, wherein the coil comprises at least one conductor spiral comprising a plurality of turns.

8. The coil assembly of claim 1, wherein the coil comprises;

a wire; or a structure made from a metal sheet.

9. The coil assembly of claim 1, wherein the coil comprises litz wire.

10. A system for transcranial magnetic stimulation, the system comprising: a pulse generator configured to generate a transcranial magnetic stimulation pulse; and a coil assembly comprising: a winding block; a coil in the winding block and a connector configured to receive the transcranial magnetic stimulation pulse and transmit the magnetic stimulation pulse to the coil; and a casing enclosing the winding block, wherein the winding block is mounted to the casing at two or more acoustic nodes of the winding block that are subject to minimal vibration during the magnetic stimulation pulse, and wherein the winding block is mounted to the casing by one or more rubber grommets and nylon bolts at the respective acoustic node, wherein each of the acoustic nodes is identified as point in the winding block having minimal amplitude of vibrations while the coil is mechanically excited during the magnetic stimulation pulse.

11. The system of claim 10, wherein an air cavity separates the winding block from the casing outside of the one or more acoustic nodes.

12. The system of claim 11, wherein the air cavity is at least partially filled with an acoustic foam.

13. The system of claim 10, wherein the casing comprises one or more sound absorbing panels.

14. The system of claim 10, wherein the casing comprises a recession under a winding center of the coil, and wherein a casing thickness of the casing is thinner within the recession than it is in at least one other region outside of the recession.

15. The system of claim 14, wherein the recession comprises a circular recession tapering from an outer diameter of the circular recession to an inner diameter of the circular recession.

16. A method for transcranial magnetic stimulation, the method comprising: generating a transcranial magnetic stimulation pulse; and supplying the magnetic stimulation pulse to a coil assembly comprising: a winding block; a coil in the winding block and a connector configured to receive the magnetic stimulation pulse and transmit the magnetic stimulation pulse to the coil; and a casing enclosing the winding block, wherein the winding block is mounted to the casing at two or more acoustic nodes of the winding block that are subject to minimal vibration during the magnetic stimulation pulse, and wherein the winding block is mounted to the casing by one or more rubber grommets and nylon bolts at the respective acoustic node, wherein each of the acoustic nodes is identified as point in the winding block having minimal amplitude of vibrations while the coil is mechanically excited during the magnetic stimulation pulse.

* * * * *